United States Patent [19]
Jeffries et al.

[11] Patent Number: 6,071,729
[45] Date of Patent: Jun. 6, 2000

[54] DISRUPTION OF THE CYTOCHROME C GENE IN XYLOSE-FERMENTING YEAST

[76] Inventors: Thomas W. Jeffries, 5517 Greening La., Madison, Wis. 53705; Nian-Qing Shi, 1 Fleischman Cir., Madison, Wis. 53719

[21] Appl. No.: 09/274,642

[22] Filed: Mar. 23, 1999

Related U.S. Application Data

[60] Provisional application No. 60/080,493, Apr. 2, 1998.
[51] Int. Cl.$^7$ ................................. C12P 7/08; C12N 1/14
[52] U.S. Cl. .............................. 435/163; 435/41; 435/93; 435/155; 435/161; 435/254.2; 435/254.23
[58] Field of Search ............................. 435/254.2, 254.23, 435/69.1, 161, 163, 41, 93, 155

[56] References Cited

U.S. PATENT DOCUMENTS 5,126,266  6/1992  Jeffries et al. ..................... 435/254.22

OTHER PUBLICATIONS

Jeppsson et al., "Existence of Cyanide–Insensitive Respiration in the Yeast *Pichia stipitis* and Its Possible Influence on Product Formation during Xylose Utilization," *Applied and Environmental Microbiology*, 61:2596–2600 (1995).

Lu et al, "Cloning and disruption of the β–isopropylmalate dehydrogenase gene (LEU2) of *Pichia stipitis* with URA3 and recovery of the double auxotroph," *Appl. Microbiol Biotechnol.* 49:141–146 (1998).

Sreenath et al., "Diminished Respirative Growth and Enhanced Assimilative Sugar Uptake Result in Higher Specific Fermentation Rates by the Mutant *Pichia stipitis* FPL–061," *Applied Biochemistry and Biotechnology* 63:109–116 (1997).

*Primary Examiner*—Remy Yucel
*Attorney, Agent, or Firm*—Michael Best & Friedrich LLP; Jill A. Fahrlander

[57] ABSTRACT

Disclosed is a xylose-fermenting mutant yeast strain exhibiting reduced expression of cytochrome c and enhanced fermentation of xylose relative to xylose-fermenting yeast strains in which cytochrome c is fully functional. Also disclosed is a method of producing ethanol from xylose by culturing a xylose-fermenting mutant yeast strain exhibiting reduced expression of cytochrome c in the presence of xylose-containing material.

21 Claims, 9 Drawing Sheets

FIG. 1

DISRUPTION OF THE CYTOCHROME C GENE IN XYLOSE-FERMENTING YEAST

CROSS-REFERENCE TO RELATED APPLICATIONS

This application claims priority to U.S. Provisional Application No. 60/080,493, filed Apr. 2, 1998.

STATEMENT REGARDING FEDERALLY SPONSORED RESEARCH OR DEVELOPMENT

This investigation was made with United States government support awarded by the following agencies:
DOE Grant Numbers: DE-AC02-83CH10093; DEFC05-92OR22072;
NIH Grant Number: HG0301;
USDA Grant Number: 96-355003172

BACKGROUND OF THE INVENTION

Within the United States, ongoing research is directed toward development of alternative energy sources to reduce our dependence on foreign oil and nonrenewable energy. The use of ethanol as a fuel has become increasingly prevalent in recent years. The current domestic use of ethanol in transportation fuels is about 1.2 billion gallons annually. In the U.S., the major portion of this is derived from the fermentation of cornstarch. Projections made by the Department of Energy indicate that by the year 2020, annual ethanol usage in fuels will have increased dramatically to an estimated 20 billion gallons. This greatly exceeds what can be economically produced from corn starch.

In order to meet the increased demand for ethanol, it will be necessary to ferment sugars from other biomass. Biomass refers to materials such as agricultural wastes, corn hulls, corncobs, cellulosic materials, and the like. Biomass from most of these sources contains xylose at a concentration of up to about 25–30% by weight. A practical, large-scale use must be found for xylose in order for biomass conversion to be economical. Several strains of wild-type or genetically modified yeast are able to produce ethanol through fermentation of xylose, and several bacteria have been genetically engineered for xylose fermentation as well. In general, industrial producers of ethanol strongly favor the use of yeast because yeast are relatively resistant to contamination and are easier to handle in large-scale processing. However, xylose fermentation methods known to the art lack commercial viability.

Xylose is used respiratively by many different yeast species, but it is fermented by only a few species. Fermentation of xylose to ethanol by wild type xylose-fermenting yeast species occurs slowly and results in low yields relative to fermentation rates and ethanol yields that are obtained with conventional yeasts in glucose fermentations. In order to improve the cost effectiveness of the xylose fermentation, it is necessary to increase the rate of fermentation and the ethanol yields obtained.

What is needed in the art is a yeast strain that is capable of fermenting xylose at higher rates to produce greater yields of ethanol relative to that typically obtained by xylose-fermenting yeast strains known to the art.

BRIEF SUMMARY OF THE INVENTION

One embodiment of the present invention is a mutant yeast strain that produces ethanol at a high rate relative to the corresponding wild-type yeast, the mutant yeast strain characterized by reduced expression of functional c type cytochrome.

Another aspect of the present invention is a method for converting xylose in a xylose-containing material to ethanol comprising the step of culturing a mutant yeast strain in a material containing xylose under suitable fermentation conditions for a period of time sufficient to allow the fermentation of xylose to ethanol, the mutant yeast strain characterized by high rates of ethanol production, relative to the corresponding wild-type yeast, and reduced expression of functional c type cytochrome.

In a preferred embodiment, the present invention is a cytochrome c disruptant mutant strain of *Pichia stipitis* that produces ethanol at a higher rate than the corresponding wild-type strain. Preferably, the cytochrome c disruptant is FPL-Shi21.

In another embodiment, the present invention is a derivative of a cytochrome c disruptant mutant strain of *Pichia stipitis* having a high rate of xylose fermentation in polysaccharide hydrolysates relative to the disruptant mutant strain from which it was derived. Preferably, the derivative of the cytochrome c disruptant is FPL-Shi22.

It is an object of the present invention to provide a cost-effective method of producing ethanol by fermentation of xylose.

It is another object of the present invention to provide a mutant yeast strain that is capable of fermenting xylose at a higher rate than can be achieved using strains currently known to the art.

Other objects, features, and advantages of the invention will be apparent from review of the specification and claims.

BRIEF DESCRIPTION OF THE SEVERAL VIEWS OF THE DRAWINGS

Figure 1:
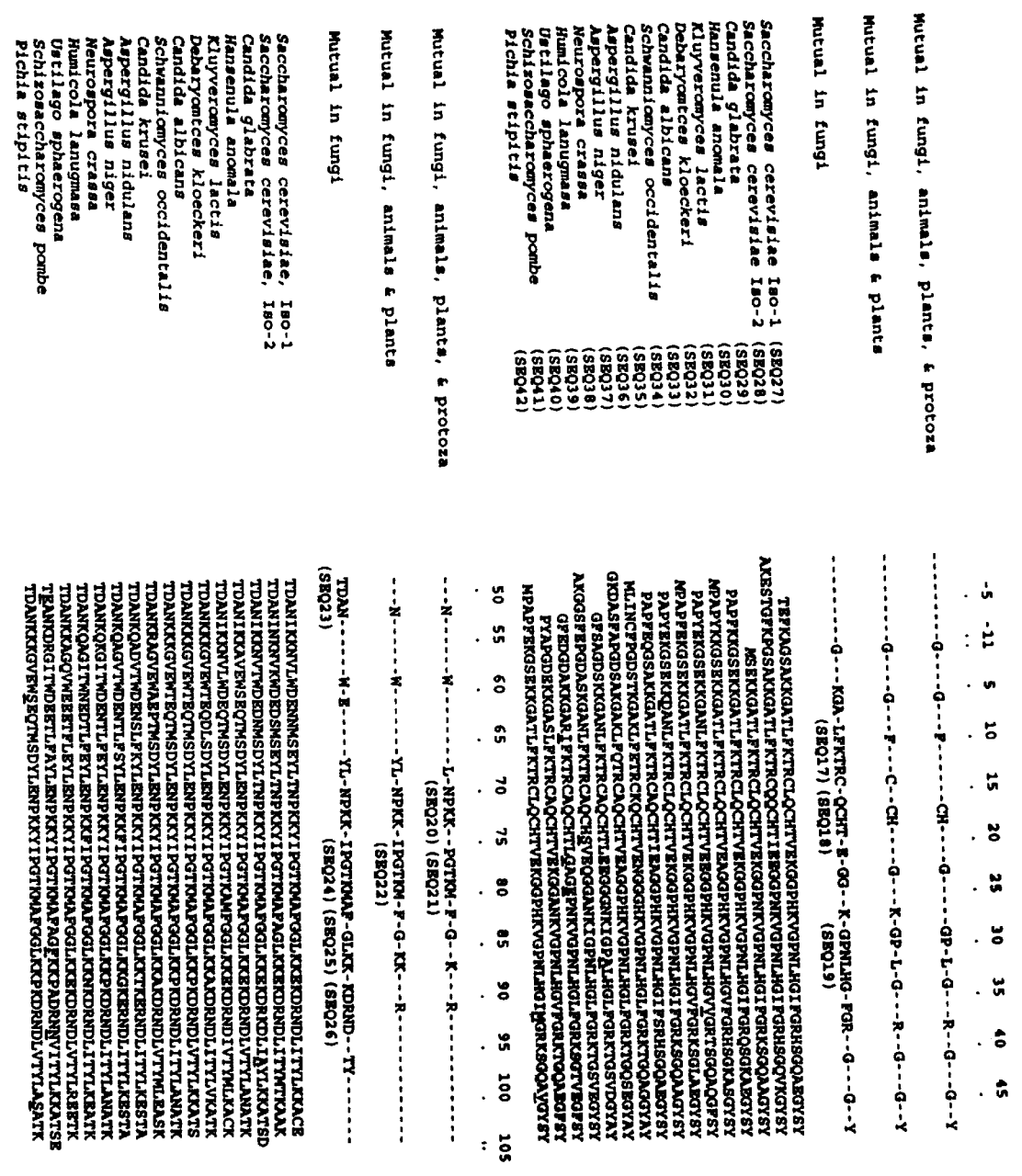

FIG. 1 shows the alignment of the amino acid sequences of cytochrome c proteins from various yeast species.

DETAILED DESCRIPTION OF THE INVENTION

Figure 2:
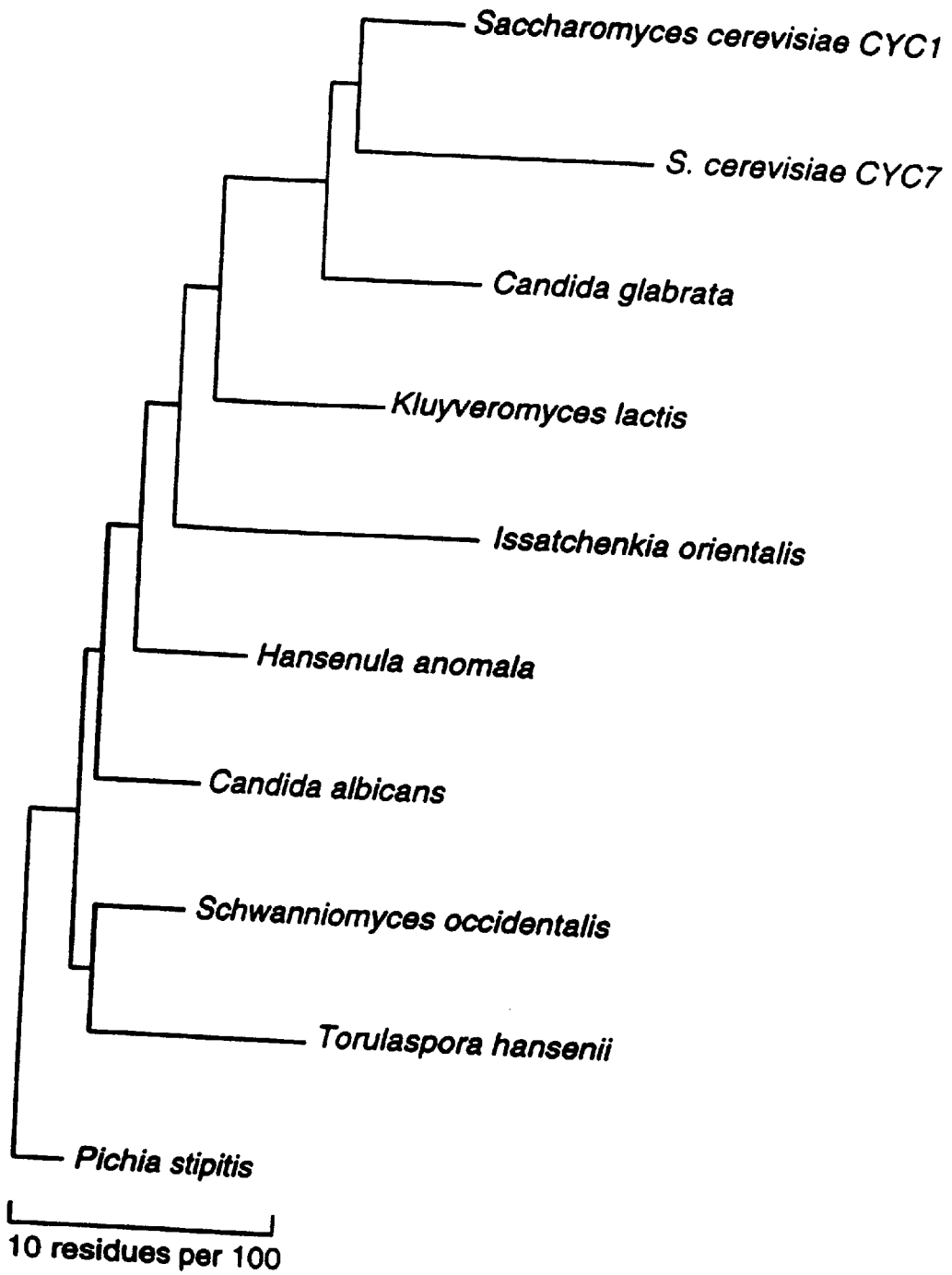
FIG. 2 is a phylogenetic tree showing the relatedness of yeast species based on homologies between cytochrome c proteins.

The present invention is a mutant yeast strain that ferments xylose at a higher rate than the corresponding wild-type yeast, the mutant yeast strain characterized by reduced expression of a functional cytochrome c gene.

The present invention is also a method of producing ethanol from the fermentation of xylose, comprising the step of: culturing a mutant yeast strain in a xylose-containing material under suitable fermentation conditions for a period of time sufficient to allow the fermentation of xylose to ethanol, the mutant yeast being capable of fermenting xylose at a high rate relative to the corresponding wild-type yeast and having reduced expression of functional cytochrome c.

Preferably, the mutant yeast strains of the present invention have specific ethanol production rates that are at least about 20% higher than the corresponding wild type yeast. More preferably, the yields are at 50%, or even 100% or more higher than the corresponding wild-type yeast.

In a preferred embodiment, the mutant yeast of the present invention is a cytochrome c disruptant mutant. By a cytochrome c disruptant mutant, it is meant a mutant in which a part or all of the functional gene is removed or replaced with DNA the expression of which does not result in a expression product having cytochrome c function.

In an alternative embodiment, expression of cytochrome c may be down-regulated through the use of an antisense construct in which part or all of the antisense strand coding for cytochrome c is expresses under the regulation of a promotor that responds to diminished oxygen. In this embodiment, the antisense mRNA for cytochrome c is expressed under oxygen limiting conditions and thereby inactivates the functional cytochrome c.

In another alternative embodiment, the promotor region for the functional cytochrome c is replaced by a promoter that responds to diminished oxygen by down-regulating expression of the cytochrome c gene.

By "wild-type" yeast, it is meant a xylose-fermenting yeast strain with normal levels of functional cytochrome c from which the mutant strain of the present invention is derived. In certain cases, the "wild-type yeast" as defined in this patent application, may include mutagenized yeast. For example, the *Pichia stipitis* strain FPL-UC7, from which FPL-Shi21 was developed, is itself a mutated yeast strain. However, FPL-UC7 is also a wild-type yeast, as defined herein, because it is a xylose-fermenting yeast with normal levels of functional cytochrome c that was used develop a mutant yeast strain of the present invention.

Many yeasts use xylose respiratively, but very few yeasts are able to ferment xylose. In yeasts capable of fermenting xylose, fermentation of xylose to ethanol occurs relatively slowly and results in lower yields compared with glucose fermentation by the same organisms.

*Pichia stipitis* is a yeast species that is able to ferment xylose to produce ethanol. In *P. stipitis*, fermentative and respirative metabolism co-exist to support cell growth and the conversion of sugar to ethanol (Ligthelem et al., *Appl. Microbiol. Biotechnol.* 28: 63–68 (1988)). *P. stipitis* differs significantly from the glucose-fermenting yeast *Saccharomyces cerevisiae* in its ability to produce ethanol from xylose. Production by wild-type *Pichia stipitis* is optimal under low aeration (Skoog and Hahn-Hägerdal, *Appl. Enviro. Microbiol.* 56: 3389–3394 (1990)). Following a shift from fully aerobic to low oxygen tension conditions, Passoth et al. (*Appl. Biochem. Biotechnol.* 57/58: 201–211 (1996)) observed no decrease in the respirative capacity, no increase in the respirative quotient ($CO_2$ production/$O_2$ consumption), and no change in the level of pyruvate dehydrogenase activity from the cells grown either on glucose or xylose. Moreover, respiration in *P. stipitis* is not repressed by the presence of fermentable sugars (Passoth et al., *Appl. Biochem. Biotechnol.* 57/58: 201–211 (1996)). Respiration in *P. stipitis* leads to diminished yields of ethanol and waste of carbon.

The constitutive respiration pattern in *P. stipitis* seemed to be peculiar until the discovery of an alternative electron transport chain that is resistant to antimycin A or cyanide but sensitive to salicyl hydroxamate (SHAM) (Jeppsson et al., *Appl. Enviro. Microbiol.* 61: 2596–2600, 1995). This SHAM-sensitive respiratory pathway is known to exist in a few other yeast species such as *Hansenula anomala* (Sakajo et al., *Biochim. Biophys. Acta* 1090: 102–108, 1990) and *Schwanniomyces castelli* (Poinsot et al., *Antonie Leeuwenhock* 53: 65–70, 1987). A model has been proposed in which the alternative pathway branches from the cytochrome pathway at the level of ubiquinone and donates electrons directly to oxygen to form water (Jeppsson et al., Supra, 1995). However, the composition and the function of this alternative respiratory pathway in supporting xylose conversion remain unknown.

Cytochrome c occupies a central point in the respiratory pathway of yeasts and other eukaryotic organisms. Cytochrome c is a small soluble heme protein that accepts electrons from the cytochrome b-c1 complex and donates electrons to the cytochrome oxidase complex. Cytochrome c proteins from more than 95 eukaryotic organisms have been studied. These proteins share extensive homology, which is indicative of the very ancient origin and conserved function of the respiratory cytochrome system (Moore and Pettigrew, *Cytochromes c: Evolutionary, Structural and Physiochemical Aspects,* Springer-Verlag, Berlin, 1990).

In order to dissect the nature of the respiratory machinery in *P. stipitis*, a mutant strain of *P. stipitis* having reduced expression of functional cytochrome c was generated, as described in detail in the examples below. Briefly, to create a mutant strain of *P. stipitis* having reduced expression of functional cytochrome c, the *P. stipitis* cytochrome c gene (PsCYC1) was cloned and sequenced as detailed in the examples below. Its DNA sequence, which is shown in SEQ ID NO:1, has been deposited in GenBank Accession number: AF 030426. A disruption cassette was created by ligating portions of the 5' and 3' flanking regions of a cloned *P. stipitis* cytochrome c gene to the 5' and 3' regions of a URA3 gene. The disruption cassette was introduced by site-specific integration into the genome of a *P. stipitis* diploid strain FPL-UC7 (Lu et al., *Appl. Environ. Biotechnol.* 49:141–149, 1998b), a ura3 auxotroph. *P. stipitis* strain FPL-UC7, which was obtained as described in detail in the examples below, is sensitive to 2-deoxy-glucose (submitted, Shi et al., *Appl. Enviro. Microbiol.,* 1999), a glucose analog that is used to screen for mutants that lack the glucose repression effect (Zimmerman, *Mol. Gen. Genet.* 154: 75–82 (1977)).

A resultant disruptant strain, designated FPL-Shi21, was obtained and has been characterized as described in detail below. The *Pichia stipitis* strain FPL-Shi21 was deposited at the Agricultural Research Service Culture Collection, 1815 North University Street, Peoria, Ill. 61604, USA Peoria, Ill. on Mar. 30, 1998 under the Budapest Treaty and was assigned accession number NRRL Y-21971.

The mutant strain FPL-Shi21 contains no heterologous or foreign DNA. FPL-Shi21 exhibits a significantly higher specific ethanol yield than FPL-UC7 when grown on xylose, despite being a slow grower relative to FPL-UC7. Under the growth conditions described in the examples, FPL-Shi21 exhibited a specific ethanol yield that is about 25% or more higher than that of FPL-UC7. Preferably, the specific ethanol yield of FPL-Shi21 is at least 50%, or even as much as two-fold, higher than that of FPL-UC7. FPL-Shi21 was found to grow in the presence of 5 mM antimycin A but not 4 mM SHAM. This differential sensitivity to antimycin A and SHAM provides a convenient selection means for the development of additional xylose fermenting mutants expressing functional cytochrome c at a reduced level. As noted in U.S. Pat. No. 5,126,266, selection for growth on non-inductive carbon sources in the presence of the respiration inhibitors SHAM and Antimycin A resulted in mutants of *Pichia stipitis* and *Candida shehatae* that could ferment mixtures of xylose and glucose at higher rates than the wild type parents. One such strain, *Pichia stipitis* FPL-061, was a progenitor of the strain FPL-Shi21 and FPL-Shi22.

Cytochrome c disruptants of *P. stipitis* were observed to have a unique colony morphology that allows these colonies to be distinguished from FPL-UC7. When grown on minimal medium containing 2% glucose, FPL-Shi21 colonies are light yellow whereas FPL-UC7 colonies are a white creamy color. After growing for about seven days on xylose-containing medium or about 8–10 days on glucose-containing medium, the FPL-Shi21 colonies assume a wrinkled appearance.

Complete elimination of c cytochrome results in greatly diminished growth rates. It is therefore harder to prepare inocula of cycl-Δ strains, and they might not compete as well with other yeasts in mixed culture. Facultative anaerobic yeasts such as *Saccharomyces cerevisiae* down-regulate expression of cyc genes when grown under oxygen limited conditions. This results in more efficient growth aerobically and more efficient fermentation anaerobically. To mimic this condition, we created an antisense construct of PsCYC1 in which the expression of the PSCYC1 antisense mRNA was controlled by an oxygen-regulated promoter from PsADH1 (Cho and Jeffries, 1998). Expression of genes driven by this promoter is increased ten-fold when cells are shifted from aerobic to oxygen-limited conditions. As more antisense PsCYC1 mRNA is expressed under oxygen-limited conditions, it binds to PSCYC1 mRNA to form an RNA-RNA complex. Production of cytochrome c is thereby reduced. Transformation of FPL-UC7 with the PsCYC1 antisense construct resulted in diminished cell growth and colonies similar to those observed with FPL-Shi21, which suggests that cytochrome c production may have been repressed.

It is expected that other cytochrome c disruptant mutants can readily be obtained using FPL-UC7, which was deposited at Agricultural Research Service Culture Collection, 1815 North University Street, Peoria, Ill. 61604, USA) on Jun. 6, 1995 under the Budapest Treaty and was assigned accession number NRRL Y-21448 or *P. stipitis* FPL-PLU20 (Lu et al., *Appl. Microbiol. Biotechnol.* 49:141–146, 1998; Cho and Jeffries, *Appl. Environ. Microbiol.* In press) as the progenitor. The *P. stipitis* strain FPL-PLU20 was deposited at Agricultural Research Service Culture Collection, 1815 North University Street, Peoria, Ill. 61604, USA on Mar. 30, 1998 under the Budapest Treaty and was assigned accession number NRRL Y-21970.

The mutant *P. stipitis* strain FPL-Shi21 was obtained by one step site-specific integration of a disruption cassette containing 584 bp of the 5' flanking region plus 56 bp of the 5' PsCYC1 coding region and 278 bp of the 3' flanking region plus 83 bp of the 3' PsCYC1 coding region of the PsCYC1 gene. It is expected that similar cytochrome c disruptants of *P. stipitis* may be obtained using a disruption cassette comprising larger or smaller portions of the 5' and 3' regions of the PsCYC1 gene or its flanking regions.

It is anticipated that a mutant strain of *P. stipitis* characterized by reduced expression of functional cytochrome c gene and increased specific ethanol yield may be obtained by means other than eliminating the cytochrome c gene by one step site-specific integration using a disruption cassette. For example, a mutant lacking functional cytochrome c, or which expresses cytochrome c at a reduced level, could be obtained by any of several means known to the art, such as exposing yeast cells to DNA-intercalating agents or irradiating yeast cells with ultra violet light. It is likely that cytochrome c deficient cells could be distinguished from wild type cells on the basis of colony size and other morphological patterns (i.e., petite size, yellow colonies with a wrinkled appearance). The cytochrome c status of putative cytochrome c deficient colonies presumptively identified on the basis of this unique phenotype could be confirmed by replica plating on a medium containing 4 mM SHAM to identify SHAM-sensitive mutants in which the cytochrome c respiratory pathway is not functioning.

In addition to *Pichia stipitis*, several other yeast species are known to employ more than one respiratory pathway. These species can be assigned to one of four groups: Group I (a cytochrome pathway and a SHAM sensitive pathway); Group II (a cytochrome pathway, an antimycin A- and SHAM-insensitive pathway, and a SHAM-sensitive pathway); Group III (an antimycin-A insensitive pathway and a cytochrome pathway), and Group IV (cytochrome c pathway). Group I includes *Pichia stipitis, Hansenula anomala, Hansenula california, Schwanniomyces castellii, Aspergillus niger*, and *Neurospora crassa*. Group II includes *Hansenula saturnus* and *Endomycopsis capsularis*. Group III includes *Schizosacchromyces pombe, Candida utilis, Candid parapilosis*, and *Kluyveromyces lactis*. Group IV includes *Hansenula glucozyma*. Among Group III members, *Candida utilis* is known to use xylose aerobically. It is anticipated that a mutant having reduced expression of functional cytochrome c may be obtained easily from any member species of Group I, II, or III. For example, one wishing to obtain such a mutant could isolate the cytochrome c gene from the target species, construct a disruption cassette having a selectable marker such as ura3, transforming a sensitive strain (e.g., a ura3 auxotrophic strain) with the cassette, and selecting for putative transformants on selection medium (e.g., medium lacking uracil. Putative disruptants could be confirmed by PCR amplification and cytochrome spectroscopy, as described in the examples.

It is expected that mutant yeast strains of the present invention can be further manipulated to achieve other desirable characteristics, or even higher specific ethanol yields. For example, the mutants could be manipulated to reduce oxygen dependence by introducing the *Saccharomyces cerevisiae* URA1 (ScURA1) gene under the control of a promoter functional in *P. stipitis*. The ScURA1 gene encodes dihydroorotate dehydrogenase, an enzyme that confers the ability to grow anaerobically. *P. stipitis* mutants comprising the ScURA1 gene have been developed and are able to grow anaerobically on glucose but not xylose. Introduction of the ScURA1 gene into a cytochrome c deficient mutant by transformation is likely to yield a strain that is capable of fermenting xylose anaerobically.

Selection of improved mutant yeast strains by passaging the mutant yeast strains on medium containing hydrolysate has resulted in improved yeast with enhanced fermentation rates. Using the teachings of the present invention, one could readily such improved strains.

By xylose-containing material, it is meant any medium comprising xylose, whether liquid or solid. Suitable xylose-containing materials include hydrolysates of polysaccharide or lignocellulosic biomass such as corn hulls, wood, paper, agricultural biproducts, and the like.

By a "hydrolysate" as used herein, it is meant a polysaccharide that has been depolymerized through the addition of water to form mono and oligosaccharide sugars. Hydrolysates may be produced by enzymatic or acid hydrolysis of the polysaccharide-containing material.

Preferably, the mutant yeast strain is able to grow under conditions similar to those found in industrial sources of xylose. The method of the present invention would be most economical when the xylose-containing material can be inoculated with the mutant yeast without excessive manipulation. By way of example, the pulping industry generates large amounts of cellulosic waste. Saccharification of the cellulose by acid hydrolysis yields hexoses and pentoses that can be used in fermentation reactions. However, the hydrolysate or sulfite liquor contains high concentrations of sulfite and phenolic inhibitors naturally present in the wood which inhibit or prevent the growth of most organisms. The examples below describe the fermentation of xylose in acid hydrolysates (or sulfite waste liquor) of hard woods and soft woods by the mutant yeast strains of the present invention. It is reasonably expected that yeast strains capable of growing in sulfite waste liquor could grow be expected grow in virtually any other biomass hydrolysate.

Ideally, after converting the xylose in a hydrolysate to ethanol, the mutant yeast strain would be recycled from the hydrolysate and used to treat additional hydrolysates.

The following nonlimiting examples are intended to be purely illustrative.

EXAMPLES

Example 1

Strains

*Escherichia coli* DH5α (Gibco BRL, Gaithersburg, Md.) and XL-1 Blue™ (Stratagene, La Jolla, Calif.) were used for routine recombinant DNA experiments. XL-1 Blue™ and SOLR™ (Stragene, La Jolla, Calif.) strains were also used in conjunction with the *P. stipitis* λ-ZAP genomic DNA library. The strains CBS 6054 (NRRL Y-1145, ATCC 58785) and FPL-UC7 (NRRL-Y-21448), (Lu et al., *Appl. Microbiol. Biotechnol.* 49: 141–146, 1998) were used in the isolation of the *P. stipitis* cytochrome c gene and in the development of mutant strains.

Many yeast species exhibit the glucose repression effect, in which the fermentation of sugars other than glucose is repressed by the presence of glucose. *Pichia stipitis* is able to convert hexose to ethanol in sugar mixtures (Kreger-van Rij, *In the Yeasts—A Taxonomic Study*, pp. 455–554, 1970); however, the cells consume glucose at a faster rate than xylose is consumed (Bicho et al., *Appl. Environ. Microbiol.* 54: 50–54, 1988). In certain strains of *P. stipitis*, xylose is not used at all until the complete utilization of glucose is reached (du Preez et al., *Appl. Microbiol. Biotechnol.* 23: 228–233, 1986). To relieve the glucose repression, a glucose analog, 2-deoxyglucose (2-DOG), is often utilized to generate mutants that will consume the alternative carbon source better (Zimmerman, *Mol. Gen. Genet.* 154: 75–82, 1977). Spontaneous mutants from *P. stipitis* NRC 5568 are able to grow on medium containing 2% 2-DOG (Pardo et al., *Can. J. Microbiol.* 38: 417–422, 1991). This group of mutants also shows increased synthesis of L-rhamnose dehydrogenase, which is usually repressed by the presence of glucose (Twerdochlib et al., *Can. J. Microbiol.* 40: 896–902, 1994) The mechanism by which 2-DOG relieves catabolite repression is unclear. However, yeasts can acquire resistance to 2-DOG, a non-metabolizable compound which is toxic to the cells. In the presence of 2-DOG, the cells contain high levels of a specific 2-deoxy-glucose-6-phosphate (2-DOG-6P) phosphatase activity (Randez-Gil, et al. Yeast 11:1233–1240, 1995) which is believed to prevent the intracellular accumulation of 2-DOG-6P. Alternately, mutant yeasts can acquire resistance to 2-DOG through the loss of hexose kinase, which converts 2-DOG into the toxic, phosphorylated intermediate.

In a *P. stipitis* wild-type strain, CBS 6054, a small degree of glucose repression is observed but xylose can be co-fermented slowly with glucose (Sreenath and Jeffries, *Appl. Biochem. Biotechnology* 63–65: 109–116, 1997). Strain FPL-DX26, a strain having reduced sensitivity to glucose repression, was obtained by NTG mutagenesis of FPL-061 and selection on 2-DOG (Sreenath and Jeffries, submitted, 1998). A uracil auxotrophic strain (FPL-UC7) was obtained by subjecting DX26 to another round of NTG mutagenesis and 5-FOA selection. However, FPL-UC7 has reduced resistance to 2-DOG relative to FPL-061 and a partial glucose repression effect is observed in UC7. When FPL-UC7 ferments a mixture of xylose and glucose, xylose is not used until glucose is consumed. *Pichia stipitis* FPL-LU20 (NRRL Y-21970) is a double auxotroph (ura3/leu2) obtained as described in Lu et al. (*Appl. Microbiol. Biotechnol.* 49:141–146, 1998) and in Cho and Jeffries, (*Appl. Environ. Microbiol.* 1998).

Example 2

Media and Growth Conditions

Yeast nitrogen base without amino acids (1.7 g/l) with 5 g/l ammonium sulfate was used for routine cultivation (YNB, Difco, Detroit, Mich.) and 20 g/l glucose were used for cultivation and transformation. Uridine was supplied at 20 mg/l for the growth of UC7. Yeast strains were cultivated at 30° C., with shaking at 100 rpm for liquid cultures. *E. coli* was routinely cultivated at 37° C. in LB media supplemented with 50 µg/ml ampicillin when required.

Example 3

Enzymes and Primers

Restriction enzymes and other DNA modification enzymes were obtained from New England Biolabs (Beverly, Mass.), Statagene (La Jolla, Calif.), Promega Corp. (Madison, Wis.), or Boehringer Mannheim Biochemicals (Indianapolis, Ind.). Reaction conditions were as recommended by the suppliers. Oligo primers were synthesized by Ransom Hill, Inc. (Romona, Calif.) and Genosys Inc. (The Woodlands, Tex.).

Example 4

Identification and Characterization of the *P. stipitis* cytochrome c gene

Yeast genomic DNA was isolated by the method described in Rose et al. (*Methods in Yeast Genetics: A Laboratory Course Manual,* Cold Spring Harbor Laboratory Press, New York, 1987). A *P. stipitis* genomic library was prepared using standard methods. A fragment of the *S. cerevisiae* cytochrome c gene (ScCYC1), obtained from plasmid pAB458, (Fetrow et al., *Proteins,* 6(4):372–81 1989) was labeled with digoxigenin and used to probe 200,000 clones from the *P. stipitis* genomic library using standard methods. Three clones that hybridize with the probe were identified, and their inserts were analyzed by restriction mapping and Southern hybridization.

The three independent, overlapping clones each contain inserts of from 6.0 to 6.6 kb. A single band, produced by the action of Cla I and Bgl II restriction enzymes, was found to hybridize with the ScCYC1 probe. The sequence of a 1200 bp region that overlaps the PsCYC1 gene was determined (SEQ ID NO:1) using standard dideoxy methods and the following primers: primer 1 (5'-ACTTGCACGGTATCATGG-3') (SEQ ID NO:3); primer 2 (5'-ACTTGTGGTTTCGGTACC-3') (SEQ ID NO:4); primer 3 (5'-CAACACGGGTCGATCCGGA-3') (SEQ ID NO:5); primer 4 (5'-TCCGGATCGACCCGTGTTG-3') (SEQ ID NO:6); and primer 5 (5'-GCGGGATCCATGCCAGCTCCATTCCG-3') (SEQ ID NO:7). This sequence, which has been deposited in Gen-Bank (Accession number: AF030426), contains a 333-bp coding region for cytochrome c, an 607 bp 5' flanking region, and a 260 bp 3' flanking region.

The DNA sequence shown in SEQ ID NO:1 differs from the sequence reported in the provisional application because certain sequencing errors were detected and corrected.

Example 5

Generation of a *P. stipitis* Cytochrome c Disruptant

A 1.5 kb PsURA3 fragment was obtained by digesting pVY2 (Yang et al., *Appl. Enviro. Microbiol.,* 60:4245–4254, 1994) with BamHI and XbaI. This fragment was subcloned into pUC19 and a recombinant plasmid designated pNQ21 containing the insert was obtained. The 5' 588 bp flanking region plus 56 bp of the coding of the region of PsCYC1 was amplified with primer 6 (5'-CCGGGATCCATCAACTCATCGACCTC-3') (SEQ ID NO:8) and primer 7 (5'CCGGGATCCGTCCTTGAACAAGGTGGC-3') (SEQ ID NO:9) (each of which contains a BamHI site) using PCR conditions described in Shi and Jeffries, 1998, *Appl. Microbiol. Biotechnol.* 50,339–3345. Standard PCR conditions were used with 50 μl reaction mixtures. PCR conditions were as follows: (1) 94° C., 2 minutes, 1 cycle; (2) 30 cycles: 94° C., 40 seconds, 60° C., 40 seconds, 72° C., 1 minute 40 seconds; then (3) 72° C., 5 minutes, 1 cycle. The reaction mixtures contained 2 mM dNTPs (5 μl), Pfu (2 μl), primers (2 μl or 5 μm) and DNA (100 ng). The fragment was digested with BamHI and cloned into the BamHI site of pNQ21 to obtain pNQ22. A fragment including 83 bp of the 3' end of the PsCYC1 coding region and 278 bp of the 3' flanking region of PsCYC1 was cloned into the KpnI/PstI sites of pUC19 to obtain pNQ13. This insert from pNQ13 was subcloned as an EcoRI/HindIII fragment into pBK(KS+) to obtain pNQ23. The same fragment was excised as a PstI-PstI fragment from pNQ23 and subcloned into the PstI site of pNQ22 to obtain pNQ26. The disruption cassette, which contains 588 bp of the 5' flanking region of PsCYC1 56 bp of the 5' PsCYC1 coding region, the PsURA3 gene, 83 bp of the 3' PsCYC1 coding region, and 278 bp of the 3' flanking region of PsCYC1, was excised from pNQ26 using SmaI and SphI.

The disruption cassette was used to transform FPL-UC7 using the lithium acetate method (Rose, et al., Supra 1990). Selection of colonies of FPL-UC7 transformants was accomplished on YNB-minimal medium containing 2% glucose. Thirty-three putative disruptant colonies were obtained. Each colony was cultured in 5 ml of YNBG liquid medium at 30° C. for 3 to 4 days. Genomic DNA was isolated from each culture, and PCR screening using primer 6 and primer 8 (5'-GAATTCGATCCACAGACACTAATTG-3') (SEQ ID NO:10) was performed to identify true disruptants.

One strain, designated FPL-Shi21, was found to have a single 2.2 kb band corresponding to the disruption cassette. This strain was identified as a homozygotic cyc disruptant. The parental strain, FPL-UC7, showed only a 0.9 kb band corresponding to the wildtype PsCYC1 gene. Loss of the PsCYC1 gene from the putative disruptant strain was confirmed by Southern hybridization of genomic DNA.

Example 6

Cell Growth Rate and Cytochrome Spectra Determination

Colonies of the cycl-Δ strain were observed to be significantly smaller than those of the parental strain (FPLUC7) when grown on xylose or glucose medium. The growth rates of FPL-Shi21 and FPL-UC7 were determined as follows. Cells grown on YNB minimal medium containing either 2% glucose or 2% xylose for 3 days were used to inoculate 25 ml of liquid medium in a 125 ml baffled flask. The cultures were then incubated at 30° C. with shaking at 160 rpm. Growth rates were determined by taking samples daily and measuring the light scattering of the samples at $OD_{600}$, and the cell yields were measured gravimetrically. Under fully aerobic condidions, the growth rate of the cycl-Δ mutant FPL-Shi21 on glucose or xylose was about 50% of the growth rate of parent strain. The lower cell mass produced by FPL-Shi21 the strain indicates that the SHAM-sensitive pathway can produce some energy to support growth. This energy probably results from the linkage to proton translocation at NADH dehydrogenase complex. Because the cell yields with the FPL-Shi21 mutant are lower than with UC7, more carbon is available for fermentation. These results suggest that the cytochrome respiratory pathway in *P. stipitis* supports primary biomass formation.

Low temperature (−196° C.) spectrophotometric recordings of the FPL-UC7 and FPL-Shi21 strains were performed in whole cells of strains grown on 1% yeast extract, 2% peptone, and 1% sucrose at 30° C. for 3 days. The absorption spectra were recorded as previously described (Hickey et al., *Gene* 105: 73–81, 1991). Mutating cytochrome c in yeast and fungi usually affects the presence of other cytochrome species (Dumont et al., 1987; Drygas et al., 1989). To investigate whether disrupting PsCYC1 leads to changes in other cytochromes, we conducted a cytochrome spectrum study to examine the cytochrome contents in the cycl-Δ mutant.

The peaks of cytochromes a, a3, b, c1 and c are located at 602.5, 558.5, 553.3, and 547.3 nm, respectively. Strain FPL-Shi21 appears completely deficient in cytochromes a, a3 and c, partially deficient in cytochrome c1, and has an increased level of cytochrome b, whereas FPL-UC7 was found to contain normal levels of cytochromes c, c1, b and a3. The disruptant strain also showed an abnormally high level of porphyrins which is a typical indicator of a cyc mutant strain. The cytochrome spectrum pattern of FPL-Shi21 resembles mutants of *Saccharomyces cerevisiae* that lack cytochrome c (Downie et al., *J. Mol. Biol.* 113: 369–384, 1977). The co-disappearance of a.a3 suggests that the cytochrome c oxidase in the *P. stipitis* mutant could not function to accept electrons. Therefore, FPL-Shi21 cells have to rely on the alternative respiratory pathway to generate aerobic energy. It has been reported that in *S. cerevisiae* mutants lacking cytochrome c are also deficient in cytochrome a.a3 due to a secondary effect of the cytochrome c deficiency (Sherman et al., 1965; Downie et al.,*J. Mol. Biol.* 113:369–384, 1977; Dumont et al., *EMBO J.* 6: 235–241, 1987). The lack or diminished levels of cytochrome a.a3 was also observed in mutants of *Neurospora crass* deficient in cytochrome c (Bottorff et al., *Yeast* 6:429–440, 1994; Drygas et al., *J. Biol. Chem.* 264: 17897–17906, 1989; Nargang et al., *J. Biol. Chem.* 263: 9388–9394, 1988).

Example 7

DNA Sequence Analysis

DNA sequence assembly, alignment, and analysis were conducted using the Genetics Computer Group sequence analysis software package (Devereux et al., *Nucleic Acids Res.* 12:387–395, 1984). BLAST searches were performed on the National Center for Biotechnology Information server. Distances were calculated as substitutions per 100 amino acids using the Kimura method (Kimura, *The Neutral Theory of Molecular Biology,* Cambridge University Press, Cambridge, 1983) following deletion of gapped regions.

The PsCYC1 gene exhibits high sequence homology to 14 other yeast and filamentous fungal cytochrome c genes (Janbon et al., *Yeast* 13: 985–999, 1997) except for four regions with very unusual amino acids (FIG. 2). Following preliminary alignment of the sequences from 18 native proteins, 1 to 11 N-terminal amino acids and 0 to 1 C-terminal amino acids were deleted from various sequences to obtain core homology for taxonomic analysis.

Figure 3:
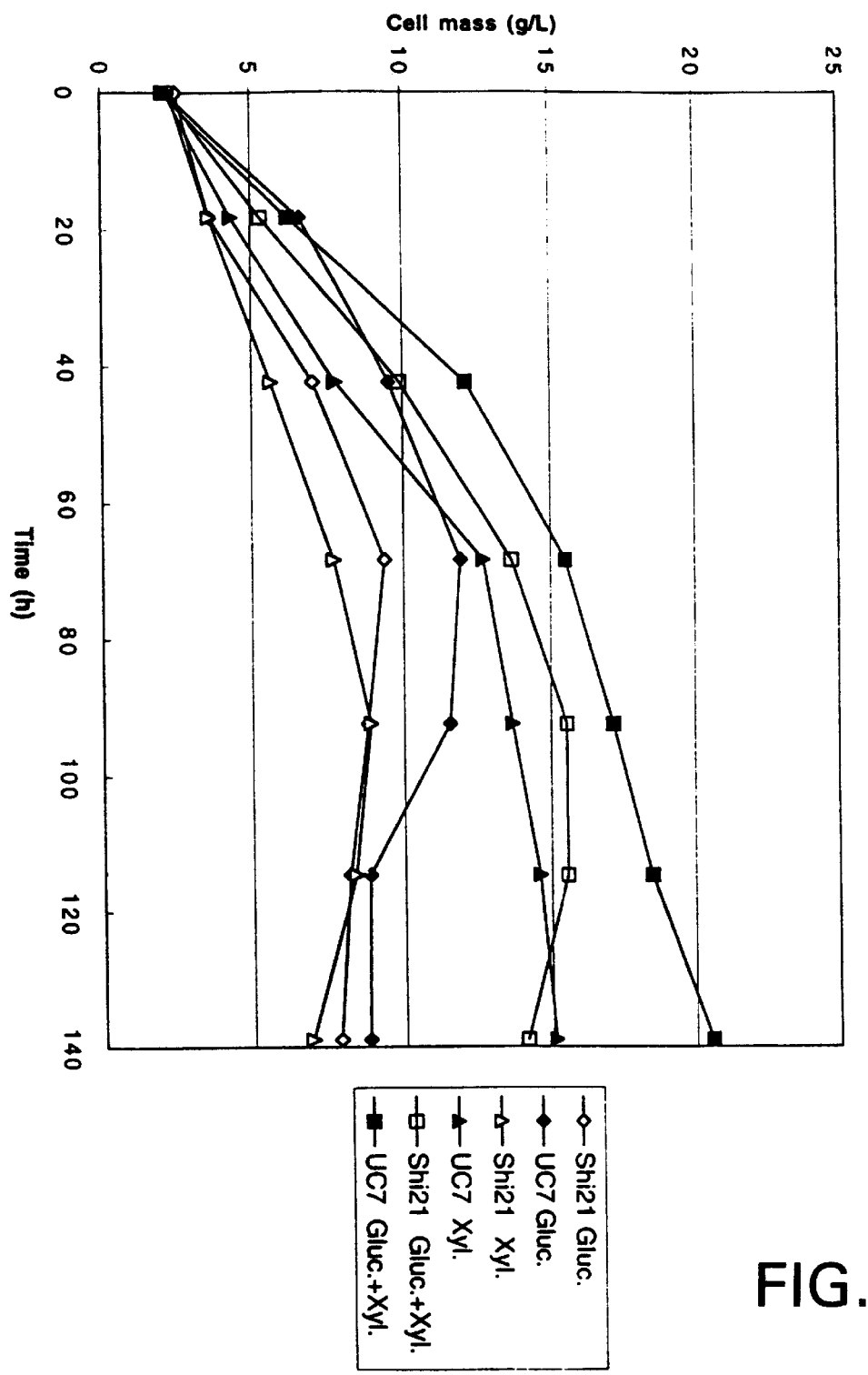
FIG. 3 shows cell growth as a function of time for FPL-Shi21 and FPL-UC7 cultivated on media containing glucose, xylose, or glucose and xylose.
Figure 4:
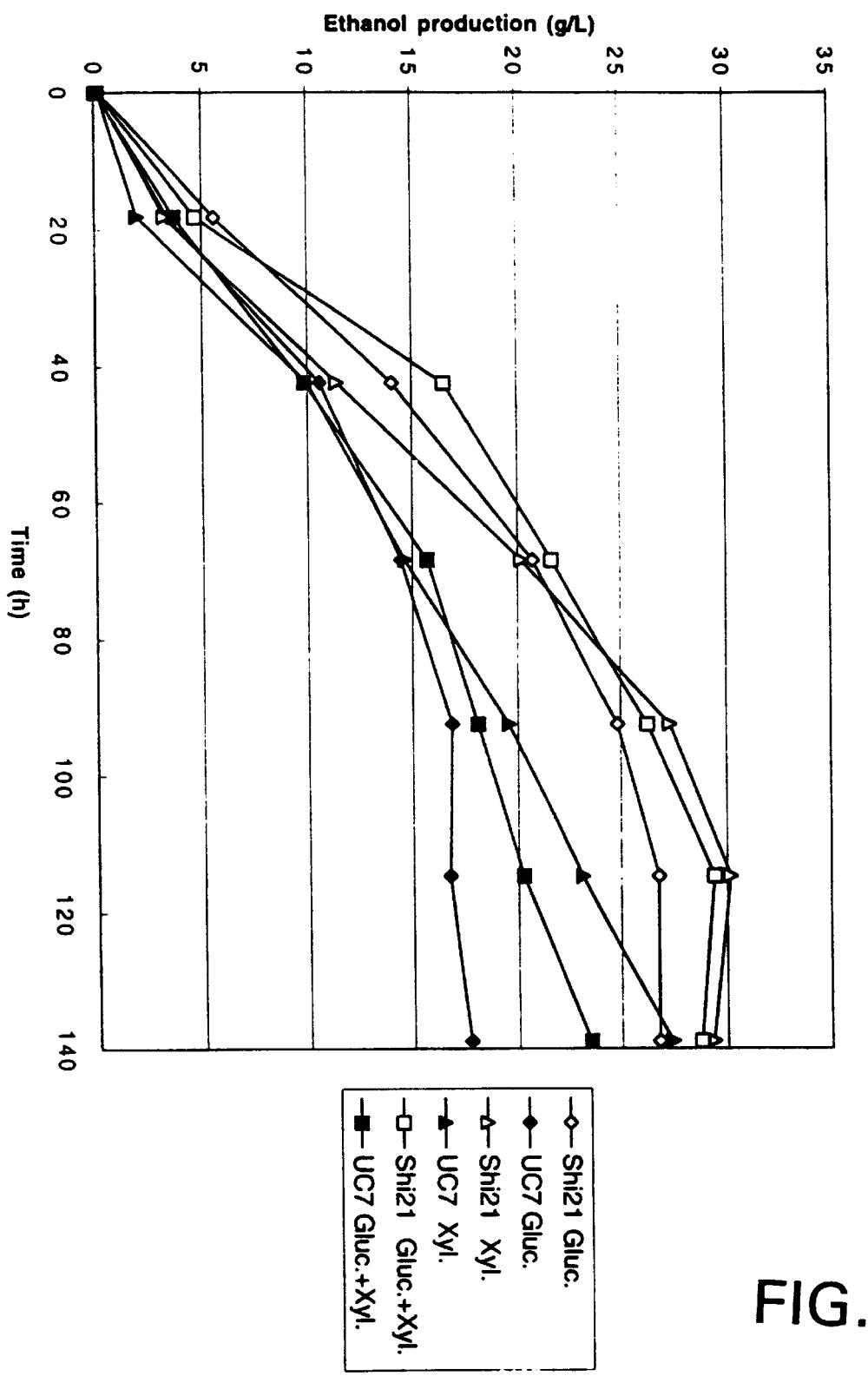
FIG. 4 shows ethanol production as a function of time for FPL-Shi21 and FPL-UC7 cultivated on media containing glucose, xylose, or glucose and xylose.

A second taxonomic analysis was performed on the sequences of 10 yeast species that showed close similarities to PsCYC1 and a phylogenetic tree constructed using the neighbor joining method (FIG. 3). The CYC sequences of the five filamentous fungi grouped together in the taxonomic analysis, but they were too distantly remote for inclusion in the phylogenetic tree. *Schizosaccharomyces pombe* was excluded from the tree due to its remote relationship with the 10 yeast CYC genes that were included. *P. stipitis* has as its apparent closest known neighbor the starch-fermenting yeast *Schwanniomyces occidentalis.*

Example 8

Possible Regulatory Elements in the PsCYC1 Gene

A single apparent TATA box is located 5' of the 333 bp cytochrome c open reading frame at −92 to −87 bp. A putative Hap1 binding site, TAATACGGTAATAT CGGACTTA (SEQ ID NO:11) located from −126 to −105 bp is strikingly similar to the ScHAP1 consensus binding sequence (Ha et al., 1996). In addition, two putative binding sites for the Hap2/3/4/5 complex, located at −152 to −144 and −136 to −128, are found to fit the consensus (Guarente, *The Molecular and Cellular Biology of the Yeast Saccharomyces: Gene Expression,* Cold Spring Harbor Laboratory Press, 49–98, 1992). The two binding sites were found clustered in a 48 bp region. The presence of HAP1 and HAP2/3/4/5 binding sites suggests that PsCYC1 expression may be regulated by oxygen mediated by heme as well as catabolite repression.

Example 9

Effect of Respiratory Inhibitors on Growth

A respiratory inhibitor study was also performed to confirm that the cycl-Δ mutant relies on the SHAM-sensitive pathway solely for aerobic energy production. Antimycin A (which blocks electron transfer from the cytochrome bc1 complex to cytochrome c) and SHAM (which blocks the electron transfer to the alternative oxidase), were used in the study. Three-day-old cells of FPL-Shi21 and FPL-UC7 were plated on YNB minimal medium containing either 2% glucose or 2% xylose supplemented with 5 $\mu$M antimycin A alone, 4 mM SHAM alone, or both respiratory inhibitors. Concentrations of the inhibitors used were determined from preliminary experiments. Cytochrome c mutant FPL-Shi21 could not grow on either xylose or glucose medium containing SHAM. The mutant FPL-Shi21 showed insensitivity to antimycin A when present alone. In contrast, the parental strain, FPL-UC7, could use either the cytochrome or the SHAM-sensitive pathway to support growth. These results demonstrate that the SHAM-sensitive pathway is the only energy-producing system in FPL-Shi21.

Interestingly, the SHAM-sensitive alternative respiration has been reported in *Schwanniomyces casetelli.* This yeast uses the alternative pathway to support glucose fermentation rather than using the cytochrome pathway. In the phylogenetic comparison with other fungal CYC genes (Example 7), PsCYC1 was found to be closest to the sole CYC gene isolated from *Schwanniomyces occidentalis.* When this yeast ferments glucose, the cytochrome pathway is repressed but not the alternative pathway (Zimer et al.,*Appl. Environ. Microbiol.* 63(7): 2779–2784, 1997).

Example 10

Ethanol Production by FPL-Shi21 and FPL UC7 and Wildtype CBS 6054

The fermentative capacity of FPL-Shi21 was tested on single or mixed sugars using FPL-UC7, CBS 6054 as a control. Yeast strains were precultured on YNB-glucose or YNB-xylose plates for 4 days. Cells were then inoculated into 25 ml of fermentation medium in a 50-ml Erlenmeyer flask. Fermentation medium contains 1.7 g/l yeast nitrogen base, 2.27 g/l urea, 6.56 g/l peptone, and 8% glucose or xylose, or 4% xylose and 4% glucose. Cultures were shaken at 100 rpm at 25 C. for 2 days. Cultures were harvested and washed once with sterile water and used as inocula for the fermentation experiments. The starting cell density was 2.5 g/l (dry weight). Samples were drawn daily and growth was determined by measuring light scattering at 600 nm. Optical densities were converted to dry weight using a previously established correlation. Then the samples were centrifuged for 10 min at 14000 rpm. The supernatant solutions were used for HPLC or GC analysis to determine the sugar composition and ethanol production rates. FPL-UC7 grew faster than FPL-Shi21 on glucose, xylose and a mixture of the two sugars (FIG. 3). However, cultures of FPL-Shi21 produced ethanol at a higher rate than cultures of UC7 even though both strains were inoculated at the same initial cell density and growth of FPL-UC7 was greater.

As reported for strains of *K. lactis* that lack cytochrome c (Chen and Clark-Walker, *Genetics*, 133: 517–525, 1993), the disruptant strain is unable to grow on glycerol, a non-fermentable carbon source.

TABLE 1

Fermentation study on 8% xylose, 8% glucose or 4% xylose +4% glucose by different strains of *P. stipitis*

| Fermentation parameters | (wild-type) CBS6054 | | | (ura3) FPL-UC7 | | | (cycl-Δ) FPL-Shi21 | | |
|---|---|---|---|---|---|---|---|---|---|
| | X | G | X + G | X | G | X + G | X | G | X + G |
| Biomass yield (YX/S)[a] | 0.17 | 0.25 | 0.23 | 0.23 | 0.26 | 0.37 | 0.12 | 0.10 | 0.19 |
| Ethanol yield (YP/S)[b] | 0.34 | 0.30 | 0.30 | 0.38 | 0.38 | 0.35 | 0.46 | 0.37 | 0.45 |
| Specific ethanol production rate (QP)[c] | 0.03 | 0.02 | 0.02 | 0.03 | 0.02 | 0.02 | 0.05 | 0.04 | 0.04 |

[a]$Y_{X/S}$ [grams (dry weight) · grams xylose$^{-1}$]
[b]$Y_{P/S}$ (grams ethanol · grams xylose$^{-1}$)
[c]$Q_E$ [grams ethanol · grams (dry weight)$^{-1}$ · h$^{-1}$]

Ethanol yield (expressed in grams ethanol/gram sugar) for FPL-Shi21 is 21% higher than that of its parent, FPL-UC7, and 35% higher than that of wild type CBS 6054 when the organisms were grown on 8% xylose. The difference in ethanol yields was even more pronounced when the organisms were grown on 4% glucose and 4% xylose. Under these conditions, the ethanol yield for FPL-Shi21 was about 29% higher than that of FPL-UC7, and 50% higher than the ethanol yield for the wild type, CBS 6054. At the same time, the cell mass of the FPL-Shi21 culture was 50% of that of FPL-UC7 or CBS 6054. The specific ethanol production rate by FPL-Shi21 using xylose, glucose or a mixture of xylose and glucose as the carbon source is 2-fold higher than that of FPL-UC7 and CBS 6054 (Table 1). FPL-Shi21 produces Ethanol 2-fold faster than its parental strains.

These observations indicated that cell mass is significantly reduced in FPL-Shi21 grown on xylose-based medium after the primary cytochrome pathway is disrupted.

FPL-Shi21 uses either xylose or glucose faster than its parental strain UC7. FPL-Shi21 had consumed all the xylose or glucose at 115 hr. UC7 utilized 80 g xylose at 139 hr and surprisingly, UC7 could not consume all the glucose during the trial. This might be attributable to mutations introduced during selection for resistance to 2-DOG. At 139 hr, 28.6 g glucose remained in the medium. In the case of the mixed sugar fermentation, UC7 and FPL-Shi21 had consumed the all the glucose at 68 hr. However, xylose was co-fermented with glucose in FPL-Shi21, but in UC7, xylose was not utilized until the glucose had been completely consumed.

FPL-Shi21 produced more ethanol on the three media types tested than its parental strain UC7 (Table 1). The highest yield of ethanol was obtained when FPL-Shi21 was grown on media containing 8% xylose. The specific ethanol yield for FPL-Shi21 grown on xylose was almost two-fold higher than that of UC7. FPL-Shi21 also displayed 80% greater specific ethanol yield than UC7 when grown on media containing 4% xylose and 4% glucose. These results suggest that the alternative pathway can support xylose conversion to ethanol. By disrupting the primary cytochrome pathway, which mainly supports biomass formation, we can significantly increase ethanol production at a specific base rate.

Example 11

Colony Morphology of *P. stipitis* FPL-Shi21 Mutant

The disruptant stain gave a phenotype and showed some very interesting changes in its appearance on plates compared to the parental strain, FPL-UC7. The colonies of the disruptant strain were light yellow in color on minimal medium containing glucose instead of white creamy color of normal colonies. The surface of a colony of the disruptant strain started to collapse and formed wrinkles after 8–10 days on medium containing either glucose or xylose.

These morphological changes observed in the *P. stipitis* cytochrome c disruptant may be caused by oxidative stress. A strain lacking functional mitochondria was previously found to have increased sensitivity to oxidants (Collinson and Dawes, *J. Gen. Microbiol.* 138:329–335, 1992). A *K. lactis* strain exposed to the respiratory inhibitor antimycin A was found to have dramatically reduced resistance to oxidants (Billard et al., *Mol gen Genet* 257:62–70, 1997).

Example 12

Construction and Use of CYC Antisense Expression Cassette

To create an antisense CYC construct, a 630 bp *P. stipitis* xylose reductase terminator fragment was first amplified by PCR from a pXOR plasmid (Dahn et al., *Appl. Biochem. Biotechnol.* 57: 267–276, 1996) using primer 8 (SEQ ID NO:10) and primer 9: 5'-TCTAACATTGTAGTATAGTTGTATAGAC-3' (SEQ ID NO:12), and then ligated to SmaI-digested pJM6 (Yang et al., *Appl. Enviro. Microbiol.* 60: 4245–4254, 1994) to obtain as pNQ12. A 598 bp fragment containing the *P. stipitis* alcohol dehydrogenase 1 (PsADH1) promoter was amplified by PCR using primer 10: 5'-TGCACTGCAGGATCCGAGGGAAAAC-3' (SEQ ID NO:13) and primer 11: 5'-GATAATTTGGATGGATCGCAGCAC-3'(SEQ ID NO:14). A 333 bp *P. stipitis* cyc gene was also amplified by PCR from pA234 (Shi et al., submitted, 1998) using primer 12: 5'-GCGGGATCCATGCCAGCTCCATTCG-3'(SEQ ID NO:15) and primer 13: 5'-GAACTTACTTGGTGGCGGAAGCC-3'(SEQ ID NO:16). The PCR products of ADH1 and cyc fragments were phosphorylated separately by the method of Ali and Steinkasserer (Bio/Technology 18: 746–750, 1995). The two fragments were mixed at an equimolar ratio and briefly ligated at room temperature. The ligation product, in which the 5'-end of ADH1 was fused to the 3'- end of CYC, served as a new template for the next round of PCR using primer 11 and primer 13. A 940-bp amplification product containing the fusion of ADH1p-AntiCYC was recovered and digested with PstI and BamHI restriction enzymes. The PstI-BamHI fragment was ligated to the PstI and BamHI sites of pNQ12 to create pNQ16. This plasmid contains a 1570 bp expression cassette comprising ADH1p-AntiCYC-XYL1t. The construction of this clone was confirmed by restriction mapping.

The plasmid pNQ16 was used to transform FPL-UC7. As a control, FPL-UC7 was transformed with pJM6, which lacks the antisense construct. Putative transformants were plated on YNB-glucose minimal medium without uridine. The majority of the transformant colonies were significantly smaller than the pJM6 control. Because antisense RNA can reduce gene expression levels from 10% to 90%, colonies of intermediate size were also selected for future comparisons.

Example 13

Softwood and Hardwood Acid Hydrolysates

Acid hydrolysates or sulfite liquors from softwood (SWD) and hardwood (HWD) were provided by Tembec. The compositions of the SWD and HWD hydrolysates were as follows. The SWD hydrolyate was made from wood comprising about 75% spruce, 20% jackpine, and 5% red/white pine. The SWD hydrolysate had a pH of about 2.5, contained 0.5% acetic acid, 2% xylose, 2% hexose. The HWD hydrolyate was made from wood comprising about 65% maple, 24% spruce, 4% beech, and 6% jackpine. The HWD hydrolysate had a pH of about 2.2, contained 1% acetic acid, 1% xylose, 3% hexose.

The hydrolysates as supplied had been previously exposed to recombinant *S. cervisiae* strains expressing XYL3 genes from *S. cerevisiae*. Fermentation by the *S. cerevisiae* strains had converted most of the hexose in the hydrolysate to ethanol to yield 13–16 grams ethanol/liter SWD hydrolysate and 8–10 grams ethanol/liter HWD hydrolysate. However, virtually all of the xylose remained in the hydrolysate. This example shows the clear superiorit of the present invention over the recombinant *S. cerevisiae* strains.

Example 14

Preparation of Media Containing Hydrolysate

The pH and sugar concentrations of the hydrolysates were measured. The pH was adjusted to pH 6.5 using CaCO$_3$. The hydrolysates were treated overnight with 2% activated charcoal under agitation to partially remove acetic acid and certain phenolic inhibitors. The sugar concentrations were again determined, and the hydrolysates were autoclaved. Solid and liquid media containing urea (2.27 g/L), peptone (6.56 g/L), YNB (1.7 g/L) and 50%, 75%, or 100% SWD or HWD hydrolysate were prepared.

Example 15

Growth of FPL-Shi21 and Fermentation of Ethanol

In order to select for xylose-fermenting yeast capable of growing on sulfite-containing medium, strain FPL-Shi21 was first grown at 30° C. on solid medium containing 50% SWD or HWD, and transfered three times to plates containing 50% SWD or HWD. The cells were then transferred to plates containing higher levels of hydrolysate for two rounds to induce further resistance to inhibitors. Yeast from the plates were used to inoculate 25 ml liquid hydrolysate medium containing 50% SWD or HWD hydrolysate. The yeast were grown with gyrorotatory agitation (100 rpm) at 30° C. for four days. The cells were then transferred to fresh medium, and the process repeated four times.

Fermentation studies were conducted in liquid medium containing 50%, 75%, or 100% HWD or SWD using unpassaged FPL-Shi21 or a derivative of FPL-Shi21 that had been subcultured (or passaged) several times to obtain a strains that had improved resistance to inhibitors present in the hydrolysate. The derivative, designated FPL-Shi22, was deposited with the Agricultural Research Service Culture Collection, 1815 North University Street, Peoria, Ill. 61604, USA on Feb. 16, 1999 under the terms of the Budapest Treaty and was assigned accession number NRRL Y-30090.

Figure 5:
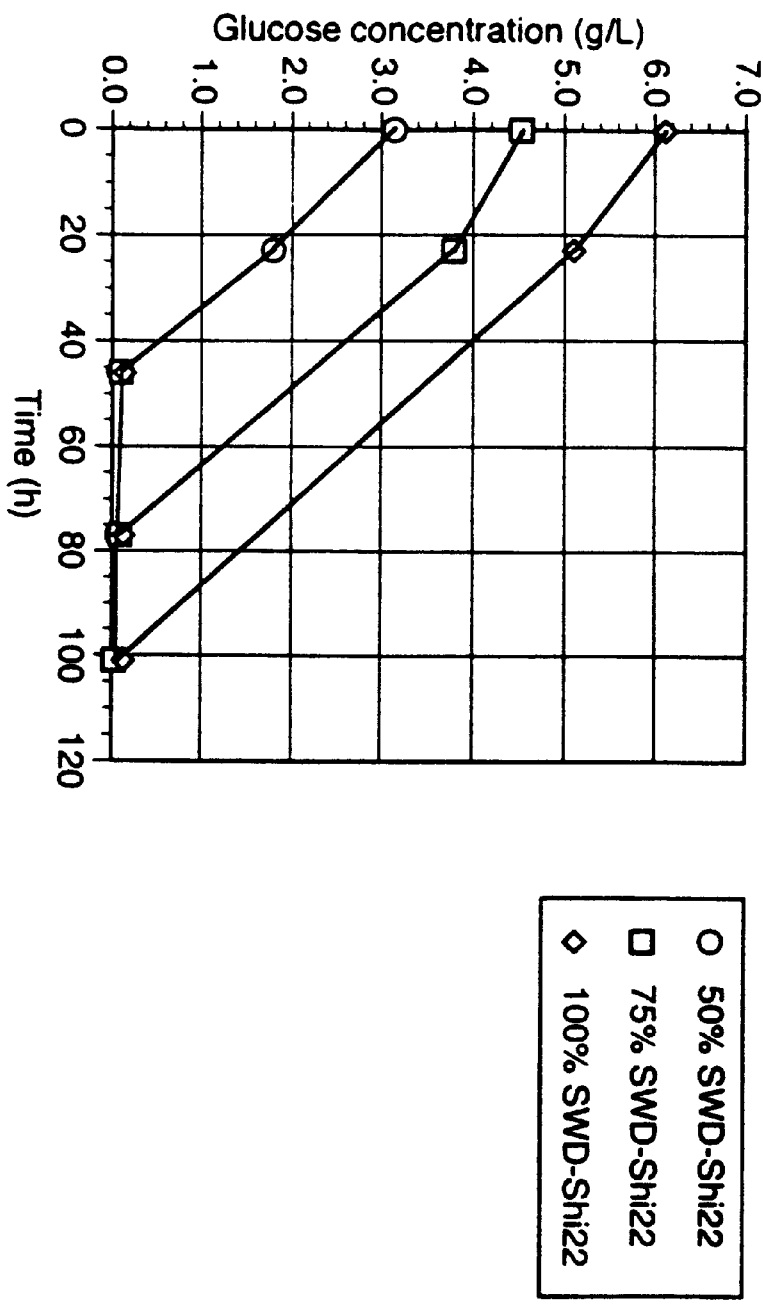
FIG. 5 shows the decrease in glucose concentration over time in FPL-Shi22 cultures prepared from softwood hydrolysates at initial concentrations of 50% (circles), 75% (squares), or 100% (diamonds).
Figure 6:
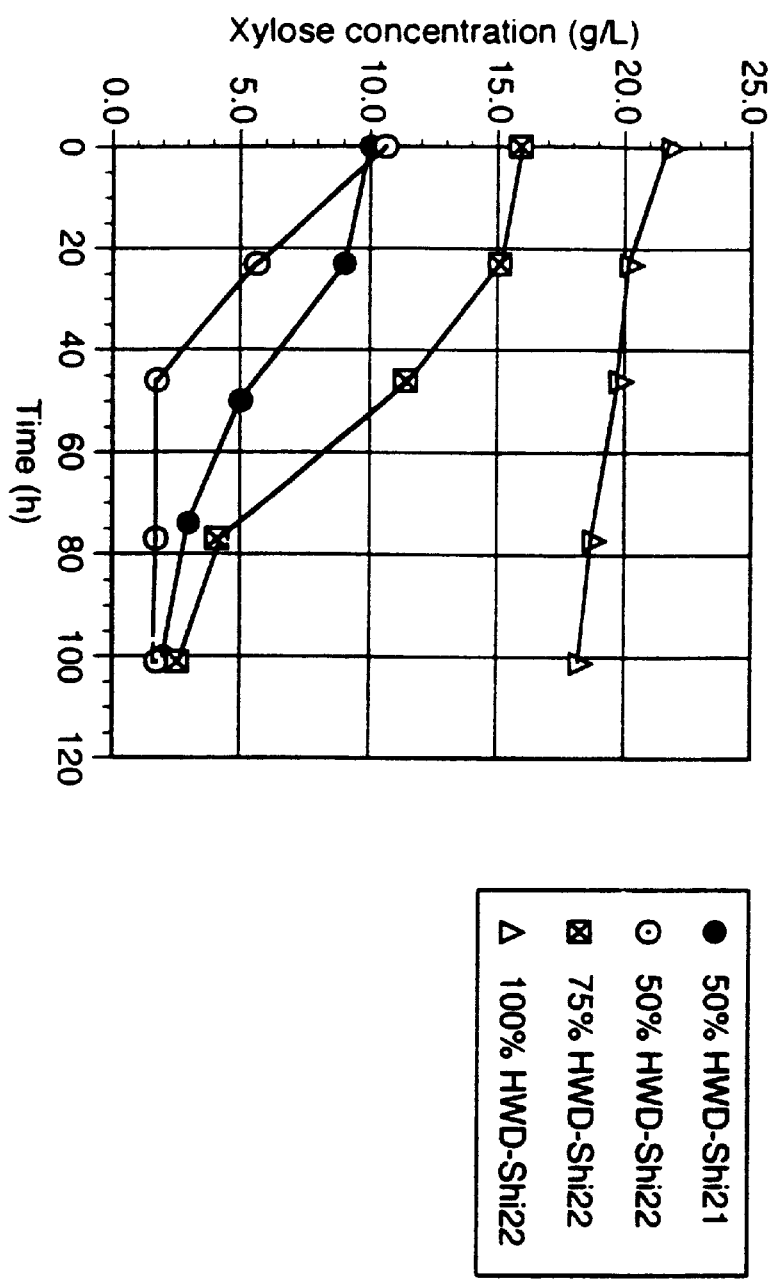
FIG. 6 shows the decrease in xylose concentration over time in FPL-Shi21 cultures prepared from hardwood hydrolysates at initial concentrations of 50% (closed circles) or FPL-Shi22 cultures prepared from hardwood hydrolysates at initial concentrations of 50% (open circles), 75% (squares), or 100% (triangles).

After inoculating the liquid medium with either FPL-Shi21 or FPL-Shi22, the yeast were cultured as described above, and the concentrations of glucose (FIG. 5), xylose (FIG. 6), and ethanol (FIG. 7) were monitored over time. Prior to being subcultured on medium containing progressively higher levels of hydrolysate, FPL-Shi21 was able to use substantially all of the xylose from only the medium containing 50% SWD. Unpassaged FPL-Shi21 could produce about 5 g ethanol/liter in 50% SWD medium, and about 2.5 g ethanol/L in the 50% HWD medium. In contrast, FPL-Shi22 was able to convert substantially all of the xylose to ethanol in media containing 50, 75, or 100% SWD or 50 or 75% HWD to give higher yields of ethanol than were obtained with FPL-Shi21. It should be noted that two different batches of hydrolysate were used to prepare media for fermentation studies using FPL-Shi21 and FPL-Shi22. Xylose concentrations may vary between different hydrolysates, as can be seen in FIG. 6.

Figure 7A:
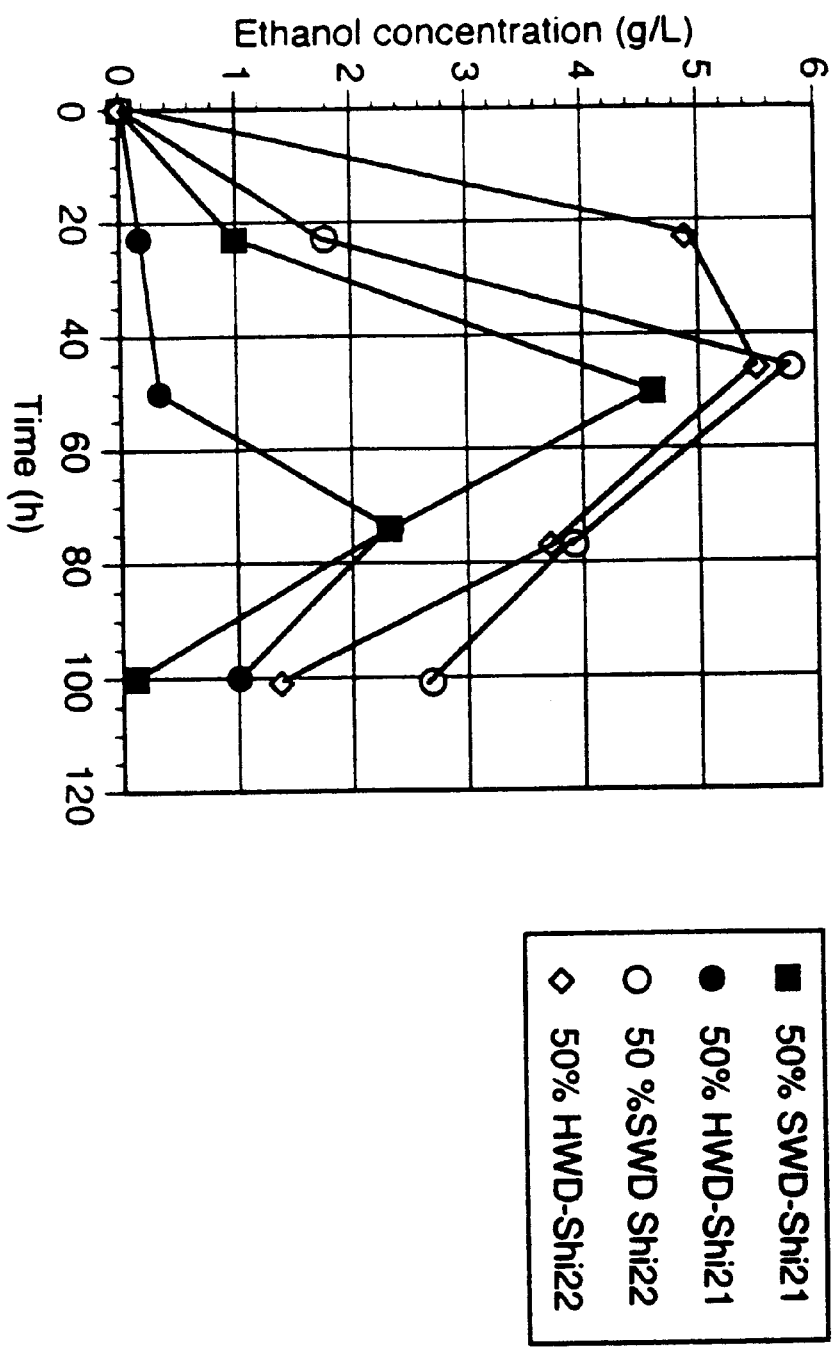
FIG. 7A shows ethanol concentrations over time in FPL-Shi21 cultures in media prepared from a softwood (squares) or hardwood (closed circles) hydrolysate at an initial concentration of 50%, or FPL-Shi22 cultures in media prepared from a softwood (open circles) or hardwood (diamonds) hydrolysate at an initial concentration of 50%.
Figure 7B:
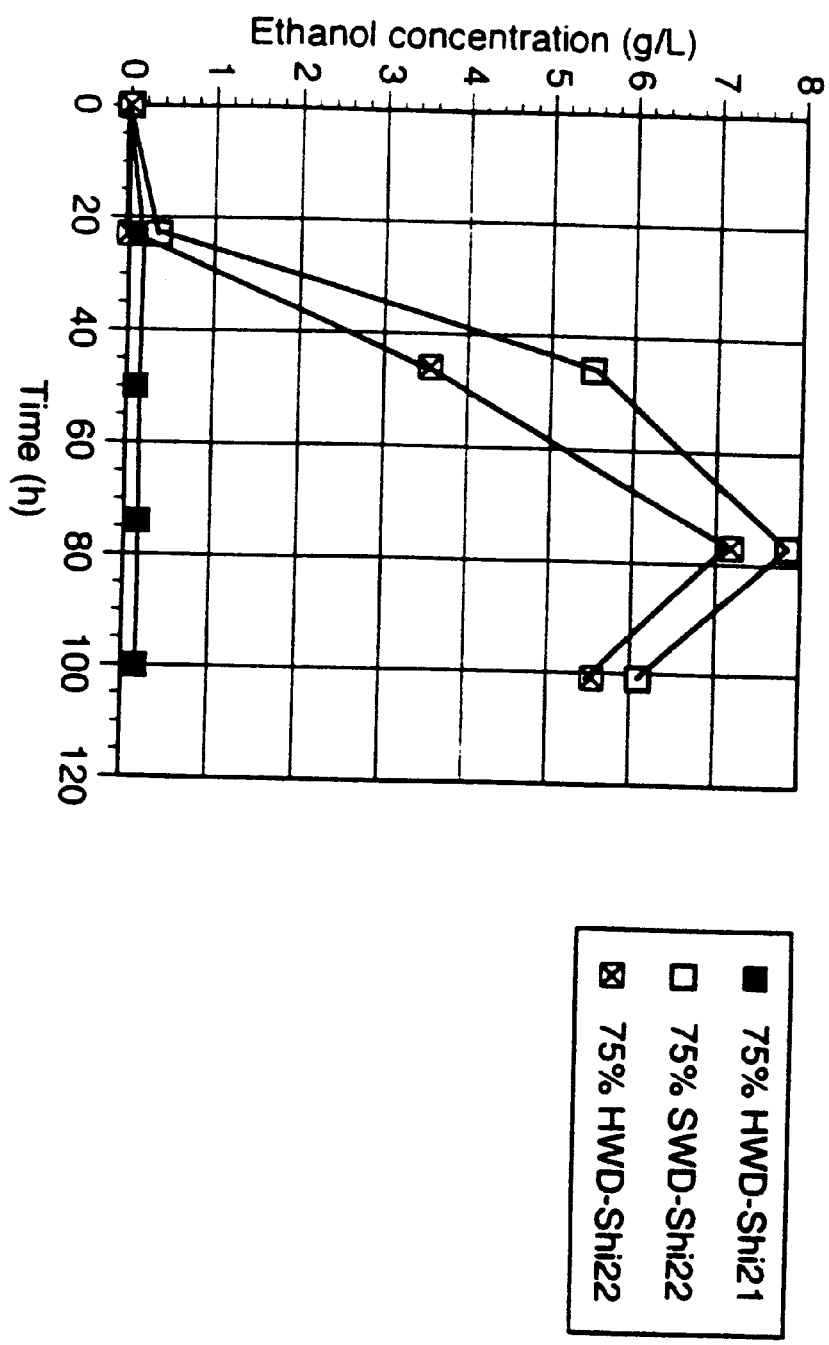
FIG. 7B shows ethanol concentrations over time in FPL-Shi21 cultures in media prepared from a hardwood (closed squares) hydrolysate at an initial concentration of 75%, or FPL-Shi22 cultures in media prepared from a softwood (open squares) or hardwood (cross-hatched squares) hydrolysate at an initial concentration of 75%.
Figure 7C:
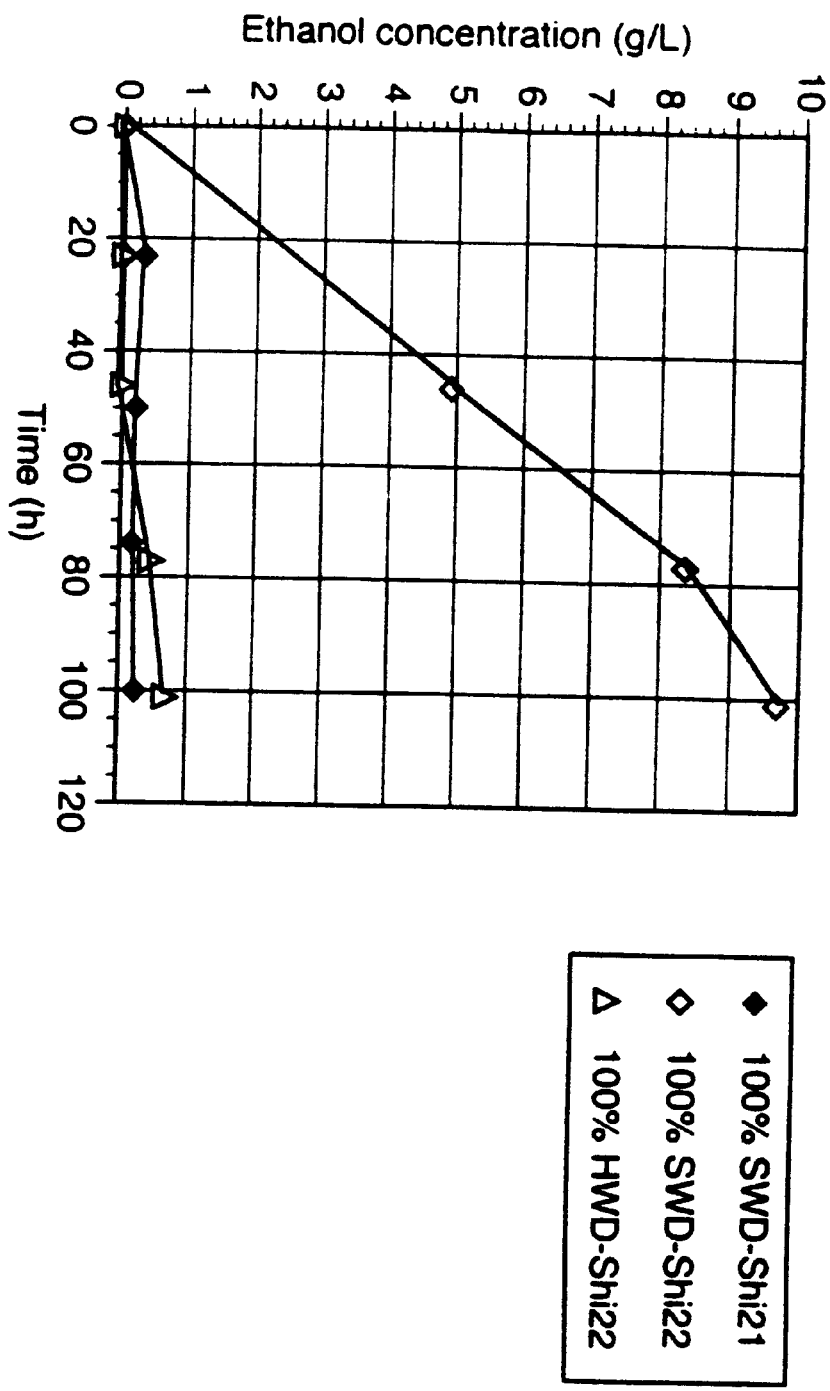
FIG. 7C shows ethanol concentrations over time in FPL-Shi21 cultures in media prepared from a softwood (closed diamonds) hydrolysate at an initial concentration of 100%, or FPL-Shi22 cultures in media prepared from a softwood (open diamonds) or hardwood (triangles) hydrolysate at an initial concentration of 100%.

As shown in FIG. 7, the mutant yeast strain FPL-Shi22 produced ethanol from 50%, 75%, and 100% SWD hydrolysates at levels of from about five to ten grams ethanol/liter. Similarly, FPL-Shi22 yeast fermented sugar present in 50% and 75% HWD hydrolysates to produce about five to seven grams ethanol/liter. Ethanol production by the FPL-Shi22 isolate grown in 100% HWD hydrolysate was very low. It is expected that continued passage of the organism on medium containing the hydrolysate will result in the isolation of an isolate capable of producing ethanol in 100% HWD hydrolysate.

All cited publications are incorporated by reference herein.

The present invention is not limited to the exemplified embodiment, but is intended to encompass all such modifications and variations as come within the scope of the following claims.

We claim:

1. A mutant yeast strain that ferments xylose to produce ethanol at a high level relative to the corresponding wild-type yeast, the mutant yeast strain having reduced expression of functional cytochrome c, relative to the corresponding wild-type yeast.

2. The mutant strain of claim 1, wherein the strain belongs to the species *Pichia stipitis*.

3. The mutant strain of claim 1, wherein the strain is a cytochrome c disruptant.

4. The mutant strain of claim 2, wherein the strain is a cytochrome c disruptant of *Pichia stipitis* FPL-UC7 (NRRL Y-21448).

5. The mutant strain of claim 1, wherein the strain is *Pichia stipitis* FPL-Shi21 (NRRL Y-21971).

6. The mutant strain of claim 1, wherein the strain is a cytochrome c disruptant of *Pichia stipitis* FPL-PLU20 (NRRL Y-21970).

7. The mutant strain of claim 1, wherein the strain has a specific ethanol production rate that is at least about 20% higher than that of the corresponding wild-type yeast.

8. The mutant strain of claim 1, wherein the strain has a specific ethanol production rate that is at least about 50% higher than that of the corresponding wild-type yeast.

9. The mutant strain of claim 1, wherein the strain has a specific ethanol production rate that is at least about 100% higher than that of the corresponding wild-type yeast.

10. An improved strain prepared from the mutant strain of claim 1, wherein the improved strain has enhanced ability to grow on hyrolysate relative to the mutant strain from which it was derived.

11. The improved strain of claim 10, wherein the derivative ferments xylose at a higher rate than the mutant strain from which it was derived.

12. The improved strain of claim 10, wherein the improved strain is FPL-Shi22 (NRRL 30090).

13. A method of producing ethanol from the fermentation of xylose, comprising the step of:
    culturing a mutant yeast strain in a xylose-containing material under suitable fermentation conditions for a period of time sufficient to allow the fermentation of xylose to ethanol, wherein the mutant yeast strain ferments xylose to produce ethanol at a high level relative to the corresponding wild-type yeast, and wherein the mutant yeast strain has reduced expression of functional cytochrome c, relative to the corresponding wild-type yeast.

14. The method of claim 13, wherein the mutant strain is *Pichia stipitis* FPL-Shi21 (NRRL Y-21971).

15. The method of claim 13, wherein the mutant strain is *Pichia stipitis* FPL-Shi22 (NRRL Y-30090).

16. The method of claim 13, wherein the xylose-containing material comprises a hydrolysate.

17. The method of claim 16, wherein the hydrolysate is an acid hydrolysate of lignocellulosic material.

18. The method of claim 16, wherein the hydrolysate is an enzymatic hydrolysate of lignocellulosic material.

19. The method of claim 13, further comprising the step of recycling the yeast from the material following the fermentation step.

20. The mutant yeast strain of claim 1, wherein reduced expression of cytochrome c in the mutant yeast is effected by a means selected from the group consisting of disruption of the cytochrome c gene and expression of antisense RNA complementary to cytochrome c mRNA.

21. The method of claim 13, wherein reduced expression of cytochrome c by the mutant yeast strain is effected by a means selected from the group consisting of disruption of the cytochrome c gene and expression of antisense RNA complementary to cytochrome c mRNA.

* * * * *

SEQUENCE LISTING

<160> NUMBER OF SEQ ID NOS: 42

<210> SEQ ID NO 1
<211> LENGTH: 1201
<212> TYPE: DNA
<213> ORGANISM: Pichia stipitis
<220> FEATURE:
<221> NAME/KEY: CDS
<222> LOCATION: (610)..(942)

<400> SEQUENCE: 1

```
aaaaatacag aaattgaatc atcaactcat cgacctcatt atcttttgca ggttaggatg     60
gaaggaacaa aacgggtcga tccggaacca aaaccgcgca ctgaaatgta cggcaaaatg    120
cacgtgacac gttcatttaa tttctgcgct catagttagc atcagagaga gtcaatattc    180
catacttaaa tgtgaaatga ataaaaatag aggctaaaca aaaagtggtt tttgctctgg    240
aaaaacgacg gaaaaattct tgaactattg aagagacaca tatggacatt tccatagttt    300
ttctttggct ttacagcgaa aatcgagtca cttttctctg ctccaaattc ctcccagtgc    360
tcgcccactc cacggcttgc ctctacagcc tattgtgcac cggattgatg tcatgacgga    420
gatttttgca ggttgtctgc acctgcacac actccatcca atgagagctc attggttagc    480
aattatggca ttattggctg aatttttcag tctgatataa aaggaagagg agttgccgaa    540
tttctggcag aagcttgttt tcttttcagt tttcctctgc tagccaatta acttcactac    600 acacaaaaa atg cca gct cca ttc gaa aag ggt tcc gaa aag aag ggt gcc    651
          Met Pro Ala Pro Phe Glu Lys Gly Ser Glu Lys Lys Gly Ala
            1               5                  10 acc ttg ttc aag acc aga tgt ttg caa tgt cac acc gtt gaa gaa ggt     699
Thr Leu Phe Lys Thr Arg Cys Leu Gln Cys His Thr Val Glu Glu Gly
 15                  20                  25                  30 ggt cct cac aag gtt ggt cct aac ttg cac ggt atc atg ggc aga aag     747
Gly Pro His Lys Val Gly Pro Asn Leu His Gly Ile Met Gly Arg Lys
                 35                  40                  45 tcc ggt caa gcc gtt ggt tac tct tac act gac gcc aac aag aag aag     795
Ser Gly Gln Ala Val Gly Tyr Ser Tyr Thr Asp Ala Asn Lys Lys Lys
             50                  55                  60 ggt gtc gaa tgg tcc gaa cag acc atg tct gac tac ttg gaa aac cca     843
Gly Val Glu Trp Ser Glu Gln Thr Met Ser Asp Tyr Leu Glu Asn Pro
 65                  70                  75 aag aag tac atc cca ggt acc aag atg gct ttc ggt ggt ttg aag aag     891
Lys Lys Tyr Ile Pro Gly Thr Lys Met Ala Phe Gly Gly Leu Lys Lys
             80                  85                  90 cct aag gac aga aac gac ttg gtc acc tac ttg gct tcc gcc acc aag     939
Pro Lys Asp Arg Asn Asp Leu Val Thr Tyr Leu Ala Ser Ala Thr Lys
 95                 100                 105                 110 taa gcggcttcca gcatagagtg aacgaaagtg ctcgcccaat atctcggtaa            992
cgaaaccact agtcaaaatc atgccttttc gttcaatgca cctgttctgc tatagattta   1052
tttcttgtaa tgccaatgag cttcaatctg gttgagtctg gagactcggc gaaacagtcg   1112
gcttgtattt cctatggtca tttcttactg tctgtacata caacatcatt caatacattc   1172
atatttatta tgtttactag taactgcaa                                     1201
```

<210> SEQ ID NO 2
<211> LENGTH: 110
<212> TYPE: PRT
<213> ORGANISM: Pichia stipitis -continued

```
<400> SEQUENCE: 2

Met Pro Ala Pro Phe Glu Lys Gly Ser Glu Lys Lys Gly Ala Thr Leu
 1               5                  10                  15

Phe Lys Thr Arg Cys Leu Gln Cys His Thr Val Glu Glu Gly Pro
             20                  25                  30

His Lys Val Gly Pro Asn Leu His Gly Ile Met Gly Arg Lys Ser Gly
         35                  40                  45

Gln Ala Val Gly Tyr Ser Tyr Thr Asp Ala Asn Lys Lys Lys Gly Val
     50                  55                  60

Glu Trp Ser Glu Gln Thr Met Ser Asp Tyr Leu Glu Asn Pro Lys Lys
 65                  70                  75                  80

Tyr Ile Pro Gly Thr Lys Met Ala Phe Gly Gly Leu Lys Lys Pro Lys
                 85                  90                  95

Asp Arg Asn Asp Leu Val Thr Tyr Leu Ala Ser Ala Thr Lys
            100                 105                 110

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:oligonucleotide

<400> SEQUENCE: 3
acttgcacgg tatcatgg                                                   18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:oligonucleotide

<400> SEQUENCE: 4
acttgtggtt tcggtacc                                                   18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:oligonucleotide

<400> SEQUENCE: 5
caacagggtc gatccgga                                                   18

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:oligonucleotide

<400> SEQUENCE: 6
tccggatcga cccgtgttg                                                  19

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence:oligonucleotide
```

-continued

<400> SEQUENCE: 7
gcgggatcca tgccagctcc attccg                26

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:oligonucleotide

<400> SEQUENCE: 8
ccgggatcca tcaactcatc gacctc                26

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence:oligonucleotide

<400> SEQUENCE: 9
ccgggatccg tccttgaaca aggtggc               27

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:oligonucleotide

<400> SEQUENCE: 10
gaattcgatc cacagacact aattg                 25

<210> SEQ ID NO 11
<211> LENGTH: 22
<212> TYPE: DNA
<213> ORGANISM: Pichia stipitis

<400> SEQUENCE: 11
taatacggta atatcggact ta                    22

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence:oligonucleotide

<400> SEQUENCE: 12
tctaacattg tagtatagtt gtatagac              28

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:oligonucleotide

<400> SEQUENCE: 13
tgcactgcag gatccgaggg aaaac                 25

<210> SEQ ID NO 14
<211> LENGTH: 24
<212> TYPE: DNA
<213> ORGANISM: Artificial Sequence

```
<220> FEATURE:
<223> OTHER INFORMATION: Description of Artificial Sequence:oligonucleotide

<400> SEQUENCE: 14
gataatttgg atggatcgca gcac                                          24

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence:oligonucleotide

<400> SEQUENCE: 15
gcgggatcca tgccagctcc attcg                                         25

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:oligonucleotide

<400> SEQUENCE: 16
gaacttactt ggtggcggaa gcc                                           23

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence:conserved
      sequence

<400> SEQUENCE: 17

Leu Phe Lys Thr Arg Cys
  1               5

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence:conserved
      sequence

<400> SEQUENCE: 18

Gln Cys His Thr
  1

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence:conserved
      sequence

<400> SEQUENCE: 19

Gly Pro Asn Leu His Gly
  1               5

<210> SEQ ID NO 20
<211> LENGTH: 4
<212> TYPE: PRT
<213> ORGANISM: Artificial Sequence
<220> FEATURE:
```

-continued

```
<223> OTHER INFORMATION: Description of Artificial Sequence:conserved
      sequence

<400> SEQUENCE: 20

Asn Pro Lys Lys
  1

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence:conserved
      sequence

<400> SEQUENCE: 21

Pro Gly Thr Lys Met
  1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence:conserved
      sequence

<400> SEQUENCE: 22

Ile Pro Gly Thr Lys Met
  1               5

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence:conserved
      sequence

<400> SEQUENCE: 23

Thr Asp Ala Asn
  1

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence:conserved
      sequence

<400> SEQUENCE: 24

Ile Pro Gly Thr Lys Met Ala Phe
  1               5

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence:conserved
      sequence

<400> SEQUENCE: 25

Gly Leu Lys Lys
  1
```

-continued

```
<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence:conserved
      sequence

<400> SEQUENCE: 26

Lys Asp Arg Asn Asp
 1               5

<210> SEQ ID NO 27
<211> LENGTH: 108
<212> TYPE: PRT
<213> ORGANISM: Saccharomyces Cerevisiae Iso-1

<400> SEQUENCE: 27

Thr Glu Phe Lys Ala Gly Ser Ala Lys Lys Gly Ala Thr Leu Phe Lys
 1               5                  10                  15

Thr Arg Cys Leu Gln Cys His Thr Val Glu Lys Gly Gly Pro His Lys
            20                  25                  30

Val Gly Pro Asn Leu His Gly Ile Phe Gly Arg His Ser Gly Gln Ala
        35                  40                  45

Glu Gly Tyr Ser Tyr Thr Asp Ala Asn Ile Lys Lys Asn Val Leu Trp
    50                  55                  60

Asp Glu Asn Asn Met Ser Glu Tyr Leu Thr Asn Pro Lys Lys Tyr Ile
65                  70                  75                  80

Pro Gly Thr Lys Met Ala Phe Gly Gly Leu Lys Lys Glu Lys Asp Arg
                85                  90                  95

Asn Asp Leu Ile Thr Tyr Leu Lys Lys Ala Cys Glu
            100                 105

<210> SEQ ID NO 28
<211> LENGTH: 112
<212> TYPE: PRT
<213> ORGANISM: Saccharomyces cerevisiae Iso-2

<400> SEQUENCE: 28

Ala Lys Glu Ser Thr Gly Phe Lys Pro Gly Ser Ala Lys Lys Gly Ala
 1               5                  10                  15

Thr Leu Phe Lys Thr Arg Cys Gln Gln Cys His Thr Ile Glu Glu Gly
            20                  25                  30

Gly Pro Asn Lys Val Gly Pro Asn Leu His Gly Ile Phe Gly Arg His
        35                  40                  45

Ser Gly Gln Val Lys Gly Tyr Ser Tyr Thr Asp Ala Asn Ile Asn Lys
    50                  55                  60

Asn Val Lys Trp Asp Glu Asp Ser Met Ser Glu Tyr Leu Thr Asn Pro
65                  70                  75                  80

Lys Lys Tyr Ile Pro Gly Thr Lys Met Ala Phe Ala Gly Leu Lys Lys
                85                  90                  95

Glu Lys Asp Arg Asn Asp Leu Ile Thr Tyr Met Thr Lys Ala Ala Lys
            100                 105                 110

<210> SEQ ID NO 29
<211> LENGTH: 104
<212> TYPE: PRT
<213> ORGANISM: Candida glabrata

<400> SEQUENCE: 29
```

```
Met Ser Glu Lys Lys Gly Ala Thr Leu Phe Lys Thr Arg Cys Leu Gln
  1               5                  10                  15

Cys His Thr Val Glu Lys Gly Pro Asn Lys Val Gly Pro Asn Leu
             20                  25                  30

His Gly Ile Phe Gly Arg Lys Ser Gly Gln Ala Ala Gly Tyr Ser Tyr
         35                  40                  45

Thr Asp Ala Asn Ile Lys Lys Asn Val Thr Trp Asp Glu Asp Asn Met
     50                  55                  60

Ser Asp Tyr Leu Thr Asn Pro Lys Lys Tyr Ile Pro Gly Thr Lys Met
 65                  70                  75                  80

Ala Phe Gly Gly Leu Lys Lys Glu Lys Asp Arg Lys Asp Leu Ile Ala
                 85                  90                  95

Tyr Leu Lys Lys Ala Thr Ser Asp
             100
```

<210> SEQ ID NO 30
<211> LENGTH: 109
<212> TYPE: PRT
<213> ORGANISM: Hansenula anomala

<400> SEQUENCE: 30

```
Pro Ala Pro Phe Lys Lys Gly Ser Glu Lys Lys Gly Ala Thr Leu Phe
  1               5                  10                  15

Lys Thr Arg Cys Leu Gln Cys His Thr Val Glu Lys Gly Gly Pro His
             20                  25                  30

Lys Val Gly Pro Asn Leu His Gly Ile Phe Gly Arg Gln Ser Gly Lys
         35                  40                  45

Ala Glu Gly Tyr Ser Tyr Thr Asp Ala Asn Ile Lys Lys Ala Val Glu
     50                  55                  60

Trp Ser Glu Gln Thr Met Ser Asp Tyr Leu Glu Asn Pro Lys Lys Tyr
 65                  70                  75                  80

Ile Pro Gly Thr Lys Met Ala Phe Gly Gly Leu Lys Lys Glu Lys Asp
                 85                  90                  95

Arg Asn Asp Leu Val Thr Tyr Leu Ala Asn Ala Thr Lys
             100                 105
```

<210> SEQ ID NO 31
<211> LENGTH: 110
<212> TYPE: PRT
<213> ORGANISM: Kluyveromyces lactis

<400> SEQUENCE: 31

```
Met Pro Ala Pro Tyr Lys Lys Gly Ser Glu Lys Lys Gly Ala Thr Leu
  1               5                  10                  15

Phe Lys Thr Arg Cys Leu Gln Cys His Thr Val Glu Ala Gly Gly Pro
             20                  25                  30

His Lys Val Gly Pro Asn Leu His Gly Val Phe Gly Arg His Ser Gly
         35                  40                  45

Lys Ala Ser Gly Tyr Ser Tyr Thr Asp Ala Asn Ile Lys Lys Asn Val
     50                  55                  60

Leu Trp Asp Glu Gln Thr Met Ser Asp Tyr Leu Glu Asn Pro Lys Lys
 65                  70                  75                  80

Tyr Ile Pro Gly Thr Lys Met Ala Phe Gly Gly Leu Lys Lys Glu Lys
                 85                  90                  95

Asp Arg Asn Asp Ile Val Thr Tyr Met Leu Lys Ala Cys Lys
             100                 105                 110
```

```
<210> SEQ ID NO 32
<211> LENGTH: 109
<212> TYPE: PRT
<213> ORGANISM: Debaryomtces kloeckeri

<400> SEQUENCE: 32

Pro Ala Pro Tyr Glu Lys Gly Ser Glu Lys Lys Gly Ala Asn Leu Phe
 1               5                  10                  15

Lys Thr Arg Cys Leu Gln Cys His Thr Val Glu Glu Gly Gly Pro His
            20                  25                  30

Lys Val Gly Pro Asn Leu His Gly Val Val Gly Arg Thr Ser Gly Gln
        35                  40                  45

Ala Gln Gly Phe Ser Tyr Thr Asp Ala Asn Lys Lys Gly Val Glu
    50                  55                  60

Trp Thr Glu Gln Asp Leu Ser Asp Tyr Leu Glu Asn Pro Lys Lys Tyr
65                  70                  75                  80

Ile Pro Gly Thr Lys Met Ala Phe Gly Gly Leu Lys Lys Ala Lys Asp
                85                  90                  95

Arg Asn Asp Leu Ile Thr Tyr Leu Val Lys Ala Thr Lys
            100                 105

<210> SEQ ID NO 33
<211> LENGTH: 110
<212> TYPE: PRT
<213> ORGANISM: Candida albicans

<400> SEQUENCE: 33

Met Pro Ala Pro Phe Glu Lys Gly Ser Glu Lys Lys Gly Ala Thr Leu
 1               5                  10                  15

Phe Lys Thr Arg Cys Leu Gln Cys His Thr Val Glu Lys Gly Gly Pro
            20                  25                  30

His Lys Val Gly Pro Asn Leu His Gly Val Phe Gly Arg Lys Ser Gly
        35                  40                  45

Leu Ala Glu Gly Tyr Ser Tyr Thr Asp Ala Asn Lys Lys Lys Gly Val
    50                  55                  60

Glu Trp Thr Glu Gln Thr Met Ser Asp Tyr Leu Glu Asn Pro Lys Lys
65                  70                  75                  80

Tyr Ile Pro Gly Thr Lys Met Ala Phe Gly Gly Leu Lys Lys Pro Lys
                85                  90                  95

Asp Arg Asn Asp Leu Val Thr Tyr Leu Lys Lys Ala Thr Ser
            100                 105                 110

<210> SEQ ID NO 34
<211> LENGTH: 109
<212> TYPE: PRT
<213> ORGANISM: Schwanniomyces occidentalis

<400> SEQUENCE: 34

Pro Ala Pro Tyr Glu Lys Gly Ser Glu Lys Lys Asp Ala Asn Leu Phe
 1               5                  10                  15

Lys Thr Arg Cys Leu Gln Cys His Thr Val Glu Lys Gly Gly Pro His
            20                  25                  30

Lys Val Gly Pro Asn Leu His Gly Ile Phe Gly Arg Lys Ser Gly Gln
        35                  40                  45

Ala Ala Gly Tyr Ser Tyr Thr Asp Ala Asn Lys Lys Lys Gly Val Glu
    50                  55                  60

Trp Thr Glu Gln Thr Met Ser Asp Tyr Leu Glu Asn Pro Lys Lys Tyr
```

```
                    65                  70                  75                  80
Ile Pro Gly Thr Lys Met Ala Phe Gly Gly Leu Lys Lys Pro Lys Asp
                85                  90                  95

Arg Asn Asp Leu Ile Thr Tyr Leu Ala Asn Ala Thr Lys
            100                 105

<210> SEQ ID NO 35
<211> LENGTH: 109
<212> TYPE: PRT
<213> ORGANISM: Candida krusei

<400> SEQUENCE: 35

Pro Ala Pro Phe Glu Gln Gly Ser Ala Lys Lys Gly Ala Thr Leu Phe
  1               5                  10                  15

Lys Thr Arg Cys Ala Gln Cys His Thr Ile Glu Ala Gly Gly Pro His
                20                  25                  30

Lys Val Gly Pro Asn Leu His Gly Ile Phe Ser Arg His Ser Gly Gln
            35                  40                  45

Ala Glu Gly Tyr Ser Tyr Thr Asp Ala Asn Lys Arg Ala Gly Val Glu
        50                  55                  60

Trp Ala Glu Pro Thr Met Ser Asp Tyr Leu Glu Asn Pro Lys Lys Tyr
 65                  70                  75                  80

Ile Pro Gly Thr Lys Met Ala Phe Gly Gly Leu Lys Lys Ala Lys Asp
                85                  90                  95

Arg Asn Asp Leu Val Thr Tyr Met Leu Glu Ala Ser Lys
            100                 105

<210> SEQ ID NO 36
<211> LENGTH: 110
<212> TYPE: PRT
<213> ORGANISM: Aspergillus nidulans

<400> SEQUENCE: 36

Met Leu Ile Asn Cys Phe Pro Gly Asp Ser Thr Lys Gly Ala Lys Leu
  1               5                  10                  15

Phe Glu Thr Arg Cys Lys Gln Cys His Thr Val Glu Asn Gly Gly Gly
                20                  25                  30

His Lys Val Gly Pro Asn Leu His Gly Leu Phe Gly Arg Lys Thr Gly
            35                  40                  45

Gln Ala Gly Gly Tyr Ala Tyr Thr Asp Ala Asn Lys Gln Ala Asp Val
        50                  55                  60

Thr Trp Asp Glu Asn Ser Leu Phe Lys Tyr Leu Glu Asn Pro Lys Lys
 65                  70                  75                  80

Tyr Ile Pro Gly Thr Lys Met Ala Phe Gly Gly Leu Lys Lys Thr Lys
                85                  90                  95

Glu Arg Asn Asp Leu Ile Thr Tyr Leu Lys Glu Ser Thr Ala
            100                 105                 110

<210> SEQ ID NO 37
<211> LENGTH: 111
<212> TYPE: PRT
<213> ORGANISM: Aspergillus niger

<400> SEQUENCE: 37

Gly Lys Asp Ala Ser Phe Ala Pro Gly Asp Ser Ala Lys Gly Ala Lys
  1               5                  10                  15

Leu Phe Gln Thr Arg Cys Ala Gln Cys His Thr Val Glu Ala Gly Gly
                20                  25                  30
```

```
Pro His Lys Val Gly Pro Asn Leu His Gly Leu Phe Gly Arg Lys Thr
         35                  40                  45

Gly Gln Ser Glu Gly Tyr Ala Tyr Thr Asp Ala Asn Lys Gln Ala Gly
 50                  55                  60

Val Thr Trp Asp Glu Asn Thr Leu Phe Ser Tyr Leu Glu Asn Pro Lys
 65                  70                  75                  80

Lys Phe Ile Pro Gly Thr Lys Met Ala Phe Gly Leu Lys Lys Gly
                 85                  90                  95

Lys Glu Arg Asn Asp Leu Ile Thr Tyr Leu Lys Glu Ser Thr Ala
             100                 105                 110

<210> SEQ ID NO 38
<211> LENGTH: 107
<212> TYPE: PRT
<213> ORGANISM: Neurospora crassa

<400> SEQUENCE: 38

Gly Phe Ser Ala Gly Asp Ser Lys Lys Gly Ala Asn Leu Phe Lys Thr
 1               5                  10                  15

Arg Cys Ala Gln Cys His Thr Leu Glu Glu Gly Gly Asn Lys Ile
             20                  25                  30

Gly Pro Ala Leu His Gly Leu Phe Gly Arg Lys Thr Gly Ser Val Asp
         35                  40                  45

Gly Tyr Ala Tyr Thr Asp Ala Asn Lys Gln Lys Gly Ile Thr Trp Asp
 50                  55                  60

Glu Asn Thr Leu Phe Glu Tyr Leu Glu Asn Pro Lys Lys Tyr Ile Pro
 65                  70                  75                  80

Gly Thr Lys Met Ala Phe Gly Leu Lys Lys Pro Lys Asp Arg Asn
                 85                  90                  95

Asp Leu Ile Thr Tyr Leu Ala Asn Ala Thr Lys
             100                 105

<210> SEQ ID NO 39
<211> LENGTH: 111
<212> TYPE: PRT
<213> ORGANISM: Humicola lanugmasa

<400> SEQUENCE: 39

Ala Lys Gly Gly Ser Phe Glu Pro Gly Asp Ala Ser Lys Gly Ala Asn
 1               5                  10                  15

Leu Phe Lys Thr Arg Cys Ala Gln Cys His Ser Val Glu Gln Gly Gly
             20                  25                  30

Ala Asn Lys Ile Gly Pro Asn Leu His Gly Leu Phe Gly Arg Lys Thr
         35                  40                  45

Gly Ser Val Glu Gly Tyr Ser Tyr Thr Asp Ala Asn Lys Gln Ala Gly
 50                  55                  60

Ile Thr Trp Asn Glu Asp Thr Leu Phe Glu Tyr Leu Glu Asn Pro Lys
 65                  70                  75                  80

Lys Phe Ile Pro Gly Thr Lys Met Ala Phe Gly Gly Leu Lys Lys Asn
                 85                  90                  95

Lys Asp Arg Asn Asp Leu Ile Thr Tyr Leu Lys Glu Ala Thr Lys
             100                 105                 110

<210> SEQ ID NO 40
<211> LENGTH: 107
<212> TYPE: PRT
<213> ORGANISM: Ustilago sphaerogena
```

<400> SEQUENCE: 40

Gly Phe Glu Asp Gly Asp Ala Lys Lys Gly Ala Arg Ile Phe Lys Thr
1               5                   10                  15

Arg Cys Ala Gln Cys His Thr Leu Gly Ala Gly Glu Pro Asn Lys Val
            20                  25                  30

Gly Pro Asn Leu His Gly Leu Phe Gly Arg Lys Ser Gly Thr Val Glu
        35                  40                  45

Gly Phe Ser Tyr Thr Asp Ala Asn Lys Lys Ala Gly Gln Val Trp Glu
    50                  55                  60

Glu Glu Thr Phe Leu Glu Tyr Leu Glu Asn Pro Lys Lys Tyr Ile Pro
65                  70                  75                  80

Gly Thr Lys Met Ala Phe Gly Gly Leu Lys Lys Glu Lys Asp Arg Asn
                85                  90                  95

Asp Leu Val Thr Tyr Leu Arg Glu Glu Thr Lys
            100                 105

<210> SEQ ID NO 41
<211> LENGTH: 108
<212> TYPE: PRT
<213> ORGANISM: Schizosaccharomyces pombe

<400> SEQUENCE: 41

Pro Tyr Ala Pro Gly Asp Glu Lys Lys Gly Ala Ser Leu Phe Lys Thr
1               5                   10                  15

Arg Cys Ala Gln Cys His Thr Val Glu Lys Gly Gly Ala Asn Lys Val
            20                  25                  30

Gly Pro Asn Leu His Gly Val Phe Gly Arg Lys Thr Gly Gln Ala Glu
        35                  40                  45

Gly Phe Ser Tyr Thr Glu Ala Asn Arg Asp Lys Gly Ile Thr Trp Asp
    50                  55                  60

Glu Glu Thr Leu Phe Ala Tyr Leu Glu Asn Pro Lys Lys Tyr Ile Pro
65                  70                  75                  80

Gly Thr Lys Met Ala Phe Ala Gly Phe Lys Lys Pro Ala Asp Arg Asn
                85                  90                  95

Asn Val Ile Thr Tyr Leu Lys Lys Ala Thr Ser Glu
            100                 105

<210> SEQ ID NO 42
<211> LENGTH: 110
<212> TYPE: PRT
<213> ORGANISM: Pichia stipitis

<400> SEQUENCE: 42

Met Pro Ala Pro Phe Glu Lys Gly Ser Glu Lys Lys Gly Ala Thr Leu
1               5                   10                  15

Phe Lys Thr Arg Cys Leu Gln Cys His Thr Val Glu Glu Gly Gly Pro
            20                  25                  30

His Lys Val Gly Pro Asn Leu His Gly Ile Met Gly Arg Lys Ser Gly
        35                  40                  45

Gln Ala Val Gly Tyr Ser Tyr Thr Asp Ala Asn Lys Lys Lys Gly Val
    50                  55                  60

Glu Trp Ser Glu Gln Thr Met Ser Asp Tyr Leu Glu Asn Pro Lys Lys
65                  70                  75                  80

Tyr Ile Pro Gly Thr Lys Met Ala Phe Gly Gly Leu Lys Lys Pro Lys
                85                  90                  95

```
-continued

Asp Arg Asn Asp Leu Val Thr Tyr Leu Ala Ser Ala Thr Lys
        100             105             110
```